US011413405B2

(12) United States Patent
Beyers et al.

(10) Patent No.: US 11,413,405 B2
(45) Date of Patent: Aug. 16, 2022

(54) INJECTION DEVICE

(71) Applicant: NOVOSANIS, Wijnegem (BE)

(72) Inventors: Koen Beyers, Wuustwezel (BE); Dimitri Willems, Putte (BE); Vanessa Vankerckhoven, Wilrijk (BE); Timothi Van Mulder, Schilde (BE); Dimitri Aslanidis, Beauvechain (BE); Stijn Verwulgen, Schoten (BE); Bart Verleije, Kalmthout (BE)

(73) Assignee: IDEVAX BV, Wijnegem (BE)

( * ) Notice: Subject to any disclaimer, the term of this patent is extended or adjusted under 35 U.S.C. 154(b) by 173 days.

(21) Appl. No.: 16/090,295

(22) PCT Filed: Apr. 3, 2017

(86) PCT No.: PCT/EP2017/057898
§ 371 (c)(1),
(2) Date: Oct. 1, 2018

(87) PCT Pub. No.: WO2017/168015
PCT Pub. Date: Oct. 5, 2017

(65) Prior Publication Data
US 2019/0111218 A1 Apr. 18, 2019

(30) Foreign Application Priority Data

Apr. 1, 2016 (EP) .................................... 16163466

(51) Int. Cl.
A61M 5/46 (2006.01)
A61M 5/32 (2006.01)
(Continued)

(52) U.S. Cl.
CPC .......... A61M 5/46 (2013.01); A61M 5/31566 (2013.01); A61M 5/32 (2013.01);
(Continued)

(58) Field of Classification Search
CPC ...... A61M 5/46; A61M 5/32; A61M 5/31566; A61M 5/326; A61M 2005/3151;
(Continued)

(56) References Cited

U.S. PATENT DOCUMENTS 3,066,670 A 12/1962 Stauffer
3,820,542 A * 6/1974 Hurschman ......... A61M 5/3243
604/196

(Continued)

FOREIGN PATENT DOCUMENTS

CN 1604799 A 4/2005
CN 1946445 A 4/2007
(Continued)

OTHER PUBLICATIONS http://hydrogen.physik.uni-wuppertal.de/hyperphysics/hyperphysics/hbase/frict2.html (Year: 2006).*

(Continued)

Primary Examiner — Lauren P Farrar
Assistant Examiner — Hamza A Darb
(74) Attorney, Agent, or Firm — Workman Nydegger

(57) ABSTRACT

An assembly for forming an injection device, comprising: a foot to be placed on a skin; a body comprising at least one needle, the body being movably mounted to the foot for allowing movement of the needle towards the skin, the needle extending out of a second contact surface by a predefined distance for limiting a penetration depth of the needle; first friction means for preventing movement of the body relative to the foot for causing a sudden acceleration; the assembly further comprising second friction means for creating a dynamic friction when the needle is moving towards the skin for keeping the skin stretched.

20 Claims, 10 Drawing Sheets

(51) Int. Cl.
  *A61M 5/315*  (2006.01)
  *A61M 5/31*  (2006.01)
(52) U.S. Cl.
  CPC .......... *A61M 5/326* (2013.01); *A61M 5/3293* (2013.01); *A61M 5/3129* (2013.01)
(58) Field of Classification Search
  CPC .... A61M 5/50; A61M 5/3129; A61M 5/3293; A61M 5/3295; A61M 5/31501; A61M 5/42; A61M 5/482
  See application file for complete search history.

(56) References Cited

U.S. PATENT DOCUMENTS

| | | | |
|---|---|---|---|
| 4,227,528 | A | 10/1980 | Wardlaw |
| 5,358,491 | A | 10/1994 | Johnson et al. |
| 5,616,128 | A | 4/1997 | Meyer |
| 7,108,679 | B2 | 9/2006 | Alchas |
| 7,250,036 | B2 | 7/2007 | Alchas |
| 7,497,841 | B2 | 3/2009 | Alchas |
| 7,569,035 | B1 | 8/2009 | Wilmot et al. |
| 7,776,013 | B2 | 8/2010 | Alchas |
| 8,162,885 | B2 | 4/2012 | Alchas |
| 8,444,606 | B2 | 5/2013 | Radmer et al. |
| 8,597,257 | B2 | 12/2013 | Modi |
| 8,632,508 | B2 | 1/2014 | Hansen et al. |
| 9,216,258 | B2 * | 12/2015 | Devereux .......... A61B 17/3478 |
| 9,242,044 | B2 | 1/2016 | Markussen |
| 9,931,472 | B2 | 4/2018 | Van Damme et al. |
| 10,850,045 | B2 | 12/2020 | Kodama et al. |
| 2002/0045858 | A1 | 4/2002 | Alchas |
| 2005/0203459 | A1 | 9/2005 | Alchas |
| 2006/0229570 | A1 | 10/2006 | Lovell et al. |
| 2007/0021719 | A1 | 1/2007 | Alchas |
| 2007/0191780 | A1 | 8/2007 | Modi |
| 2008/0015521 | A1 | 1/2008 | Alchas |
| 2008/0287883 | A1 | 11/2008 | Radmer et al. |
| 2008/0312591 | A1 | 12/2008 | Harrison |
| 2009/0192486 | A1 | 7/2009 | Wilmot et al. |
| 2009/0204102 | A1 | 8/2009 | Alchas |
| 2010/0179485 | A1 | 7/2010 | Radmer et al. |
| 2010/0241066 | A1 | 9/2010 | Hansen et al. |
| 2010/0280460 | A1 | 11/2010 | Markussen |
| 2010/0305544 | A1 | 12/2010 | Alchas |
| 2011/0319834 | A1 | 12/2011 | Modi |
| 2013/0150799 | A1 | 6/2013 | Radmer et al. |
| 2013/0211330 | A1 | 8/2013 | Pedersen et al. |
| 2014/0207078 | A1 | 7/2014 | Modi |
| 2014/0296825 | A1 * | 10/2014 | Lemaire .................. A61M 5/46 604/506 |
| 2015/0073344 | A1 | 3/2015 | Van Damme et al. |
| 2015/0273152 | A1 | 10/2015 | Modi et al. |
| 2017/0021112 | A1 | 1/2017 | Kodama et al. |

FOREIGN PATENT DOCUMENTS

| | | |
|---|---|---|
| CN | 101068586 A | 11/2007 |
| CN | 101454034 A | 6/2009 |
| CN | 104684602 A | 6/2015 |
| EP | 1722843 B1 | 9/2010 |
| EP | 2438941 A1 | 4/2012 |
| EP | 2554207 A1 | 2/2013 |
| EP | 2844317 A1 | 3/2015 |
| ES | 2351986 T3 | 2/2011 |
| GB | 2482241 A | 1/2012 |
| JP | 07505563 A | 6/1995 |
| JP | H07148258 A | 6/1995 |
| JP | H11500938 A | 1/1999 |
| JP | 2007528274 A | 10/2007 |
| JP | 2008500853 A | 1/2008 |
| JP | 2009125312 A | 6/2009 |
| JP | 2009526575 A | 7/2009 |
| JP | 2010532243 A | 10/2010 |
| JP | 2015514486 A | 5/2015 |
| JP | WO2015151516 A1 | 4/2017 |
| WO | 2003068290 A2 | 8/2003 |
| WO | 2007002052 A2 | 1/2007 |
| WO | 2007093051 A1 | 8/2007 |
| WO | 2011122395 A1 | 10/2011 |
| WO | 2012022810 A2 | 2/2012 |
| WO | 2012158135 A1 | 11/2012 |
| WO | 2013156524 A1 | 10/2013 |

OTHER PUBLICATIONS

Extended European Search Report from EP Application No. EP 16163466, dated Sep. 20, 2016.
International Search Report and Written Opinion from PCT Application No. PCT/EP2017/057898, dated Jul. 12, 2017.
First Office Action from corresponding Chinese Patent Application No. 201780022990.0, dated Jul. 22, 2020.
Office Action from corresponding Indian Patent Application No. 201827040785, dated Nov. 24, 2020.
Office Action from corresponding Japanese Patent Application No. 2018-551995, dated Mar. 2, 2021.
Office Action from corresponding Brazilian Application No. 112018070046-0, dated Dec. 9, 2021.
Office Action from corresponding Japanese Application No. 2018-551995, dated Jan. 18, 2022.

* cited by examiner

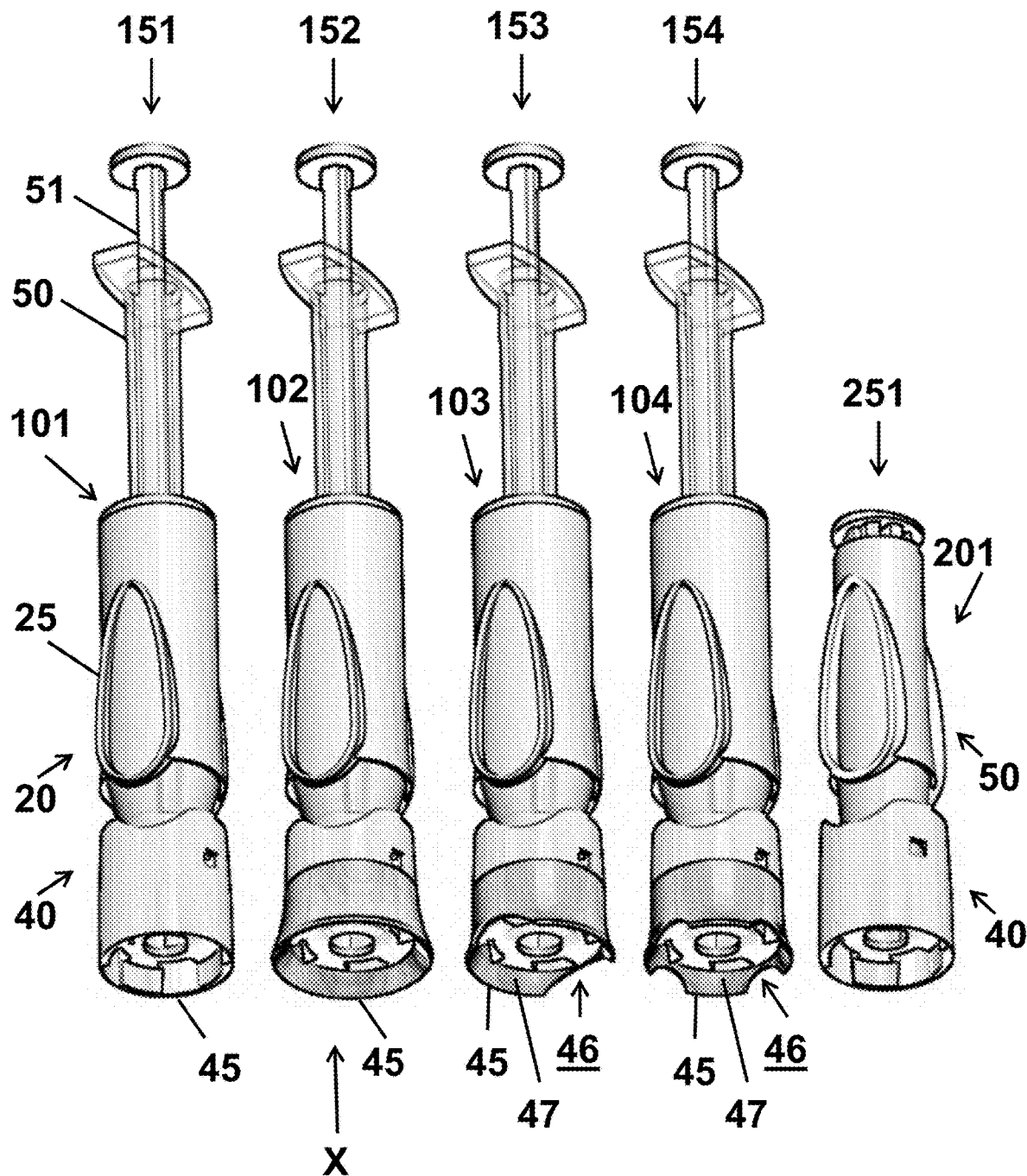

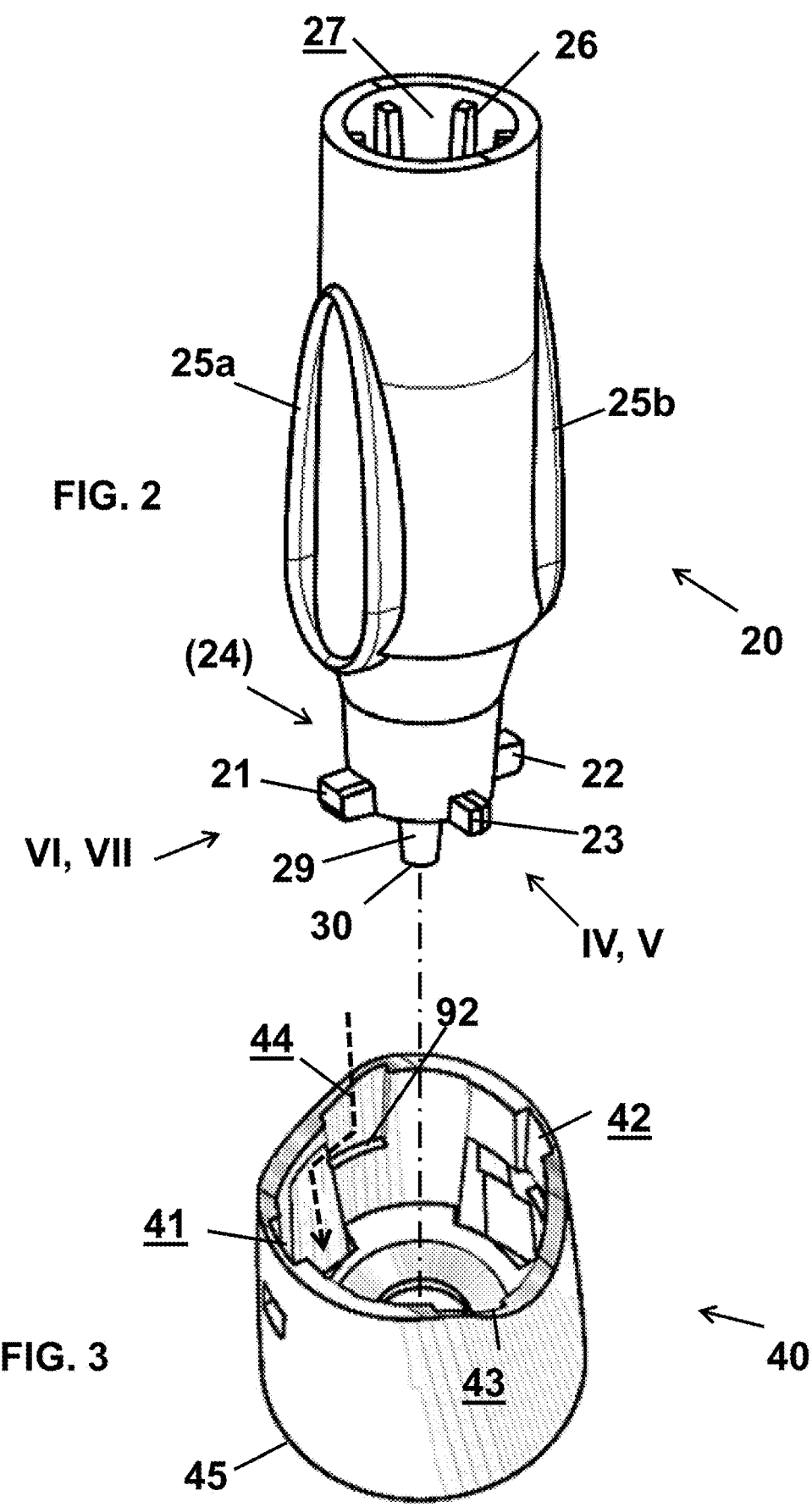

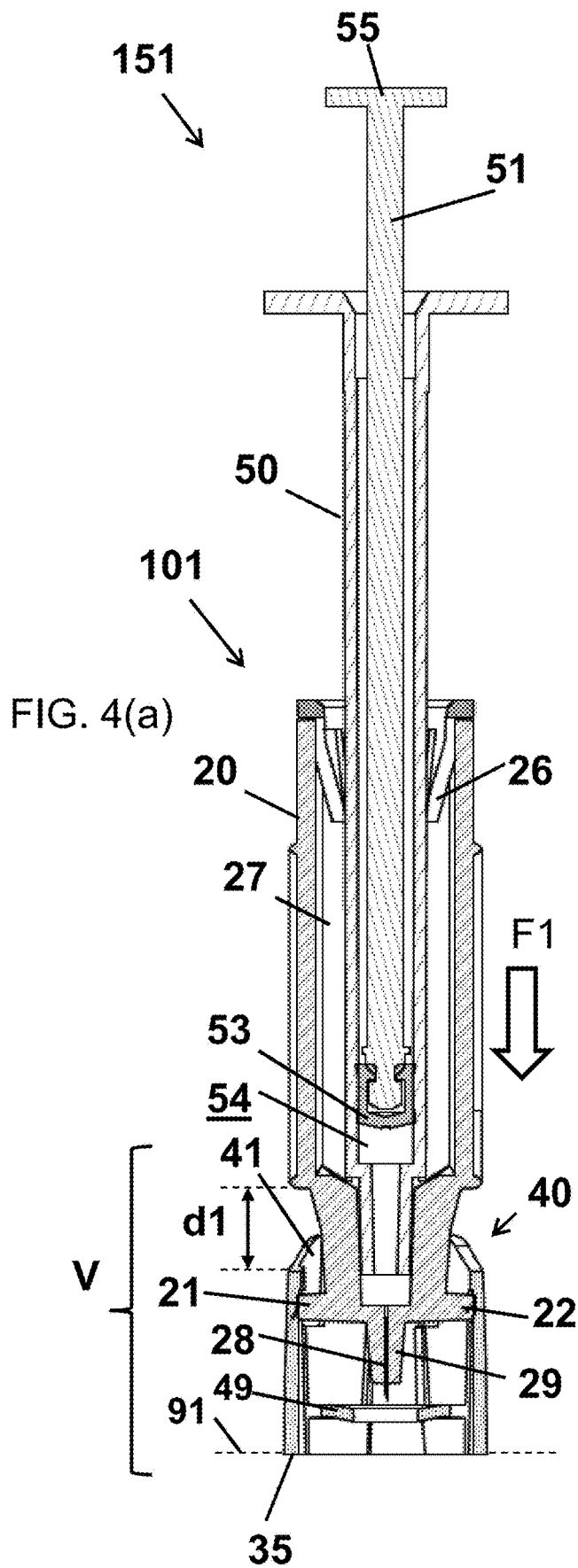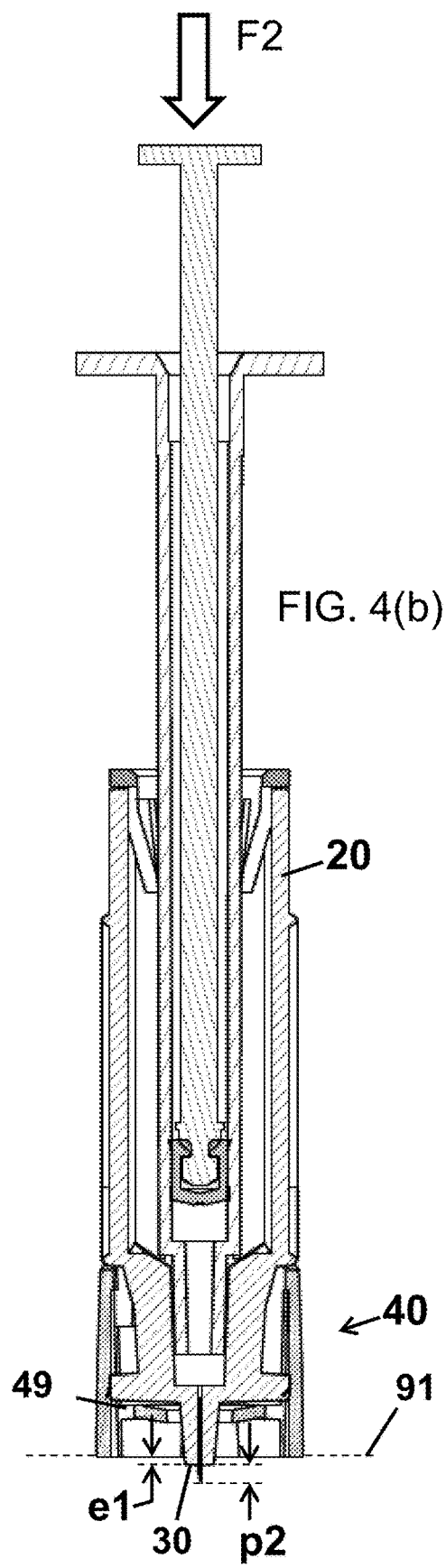

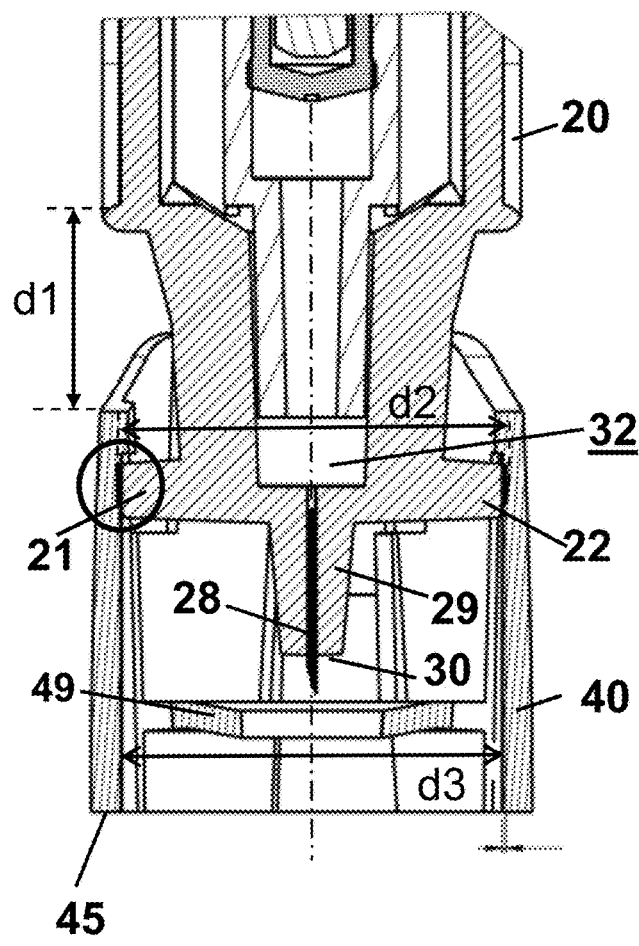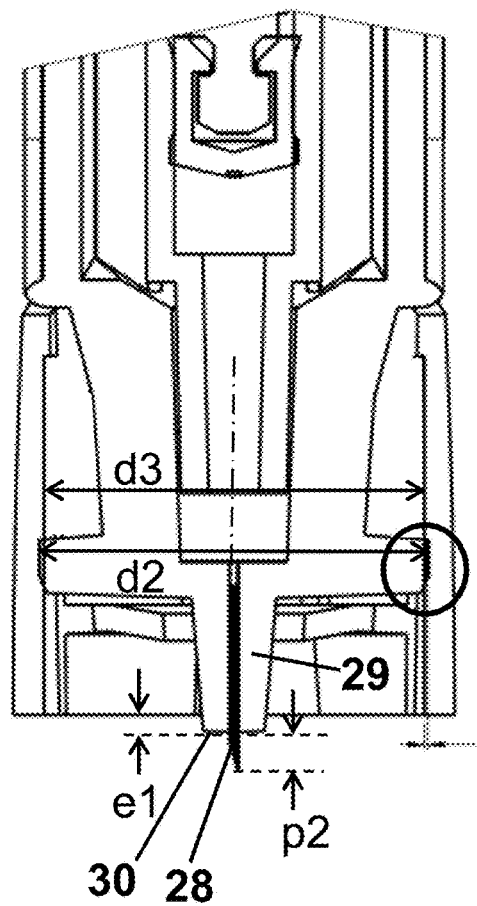
d2>d3
static+dyn friction
FIG. 5(a)
d2>d3
static+dyn friction
FIG. 5(b)

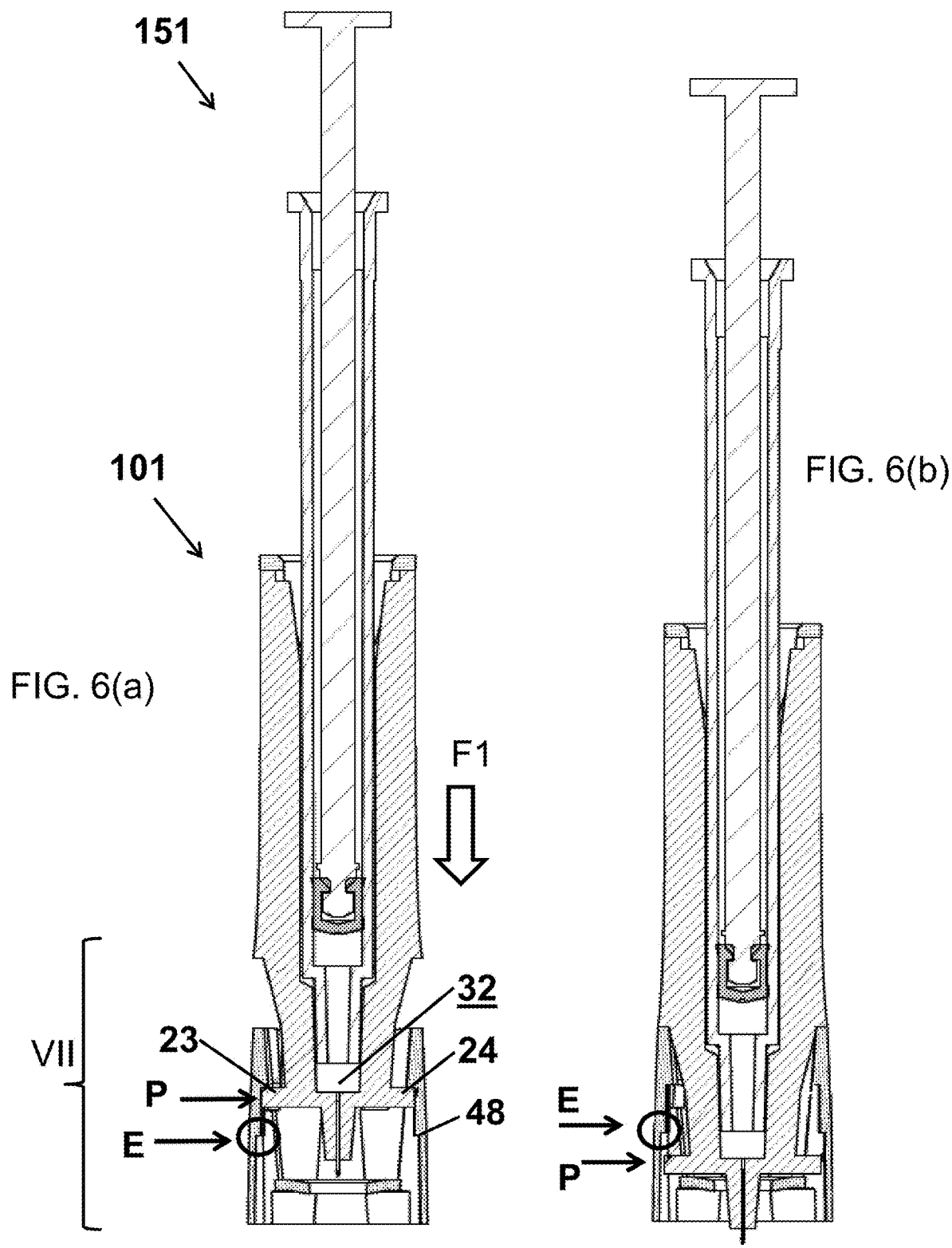

FIG. 11(a)
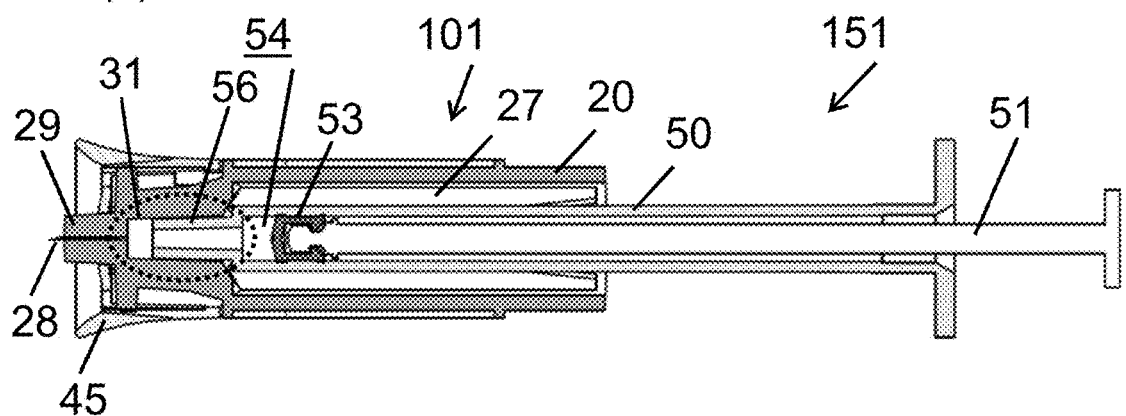
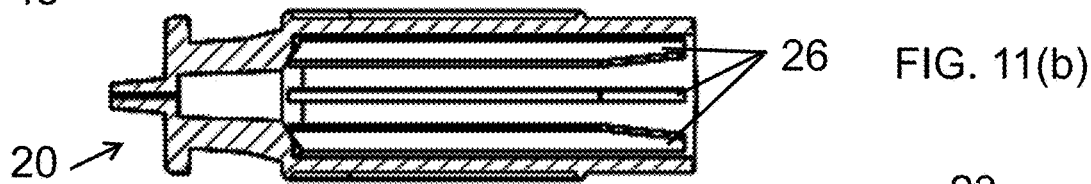
FIG. 11(b)
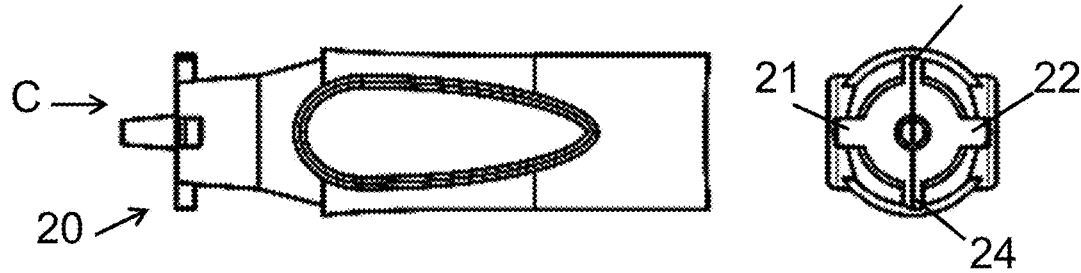
FIG. 11(c)  FIG. 11  FIG. 11(d)
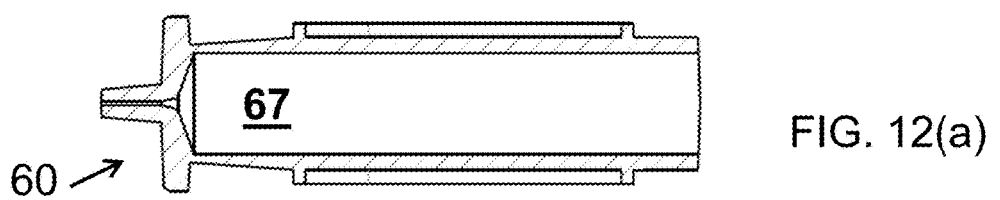
FIG. 12(a)
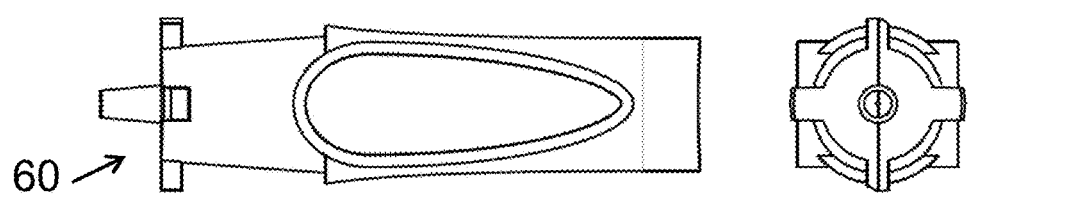
FIG. 12(b)  FIG. 12(c)

INJECTION DEVICE

FIELD OF THE INVENTION

The present invention relates to the field of injection devices. More in particular, the present invention relates to an assembly for forming an injection device for administering a fluid to a subject, and to an injection device comprising such an assembly.

BACKGROUND OF THE INVENTION

A large variety of injection devices are known in the art. The most well-known being a classical plastic medical syringe, fitted with a detachable stainless steel needle. According to the World Health Organisation, about 90% of the medical syringes are used to administer drugs, 5% for vaccinations and 5% for other uses.

Classical syringes are being used for various injection depths, such as e.g. ID (intradermal), IV (intravenous) or SC (subcutaneous) or IM (intramuscular) injections. These syringes offer the advantage of having a simple structure, being relatively cheap to produce, medical grade but they offer no additional functionality such as e.g. a mechanism for controlled penetration of the skin to a predefined depth. Correct use of classical syringes depends completely on the skills and experience of the person using the syringe. A growing number of more sophisticated injection devices is being built over the years, aimed at addressing one or more of such "additional functions".

One such highly-sophisticated device is described in WO2013156524(A1). It contains a foot to be placed on a skin, and a double-ended moveable needle, and a reservoir or a container containing a fluid to be administered. The device has a highly sophisticated mechanism to guarantee a specific sequence of events, wherein first, the device needs to be unlocked, then one first end of the needle enters the reservoir, then the reservoir and needle move inside the device and a second end of the needle penetrates the skin, subsequently the reservoir is emptied, and finally the needle is retracted. This device is ideally suited for intradermal injections.

Another sophisticated injection device is a device called DebioJect™ from the company Debiotech. It contains a foot to be placed on a skin, two cylinders, a movable needle, and a compression spring to force the needle into the skin when the spring is released. A disadvantage of this device seems to be that it requires two hands for administering a fluid: one for holding the device, another for activating the device, hence making the device not very well suited for self-administration of a fluid.

EP1722843(B1) describes an intradermal injection device having a movable sheath, which is retained by a projection, for selectively allowing the needle to extend over a relatively large distance for allowing insertion of the needle in a vial, or a short distance for penetrating a skin. In both cases the needle extends out of the sheath.

US2002045858A1 describes an intradermal delivery device with a movable enclosure means with a locking means for locking the needle in a retained position after administration of a fluid.

US2014296825(A1) describes a method and device for inserting needles, using complex driving means.

There is always room for improvements or alternatives.

SUMMARY OF THE INVENTION

It is an object of the present invention to provide an assembly and an injection device comprising same, which provides an accurate penetration depth of the needle in the skin, especially for intradermal injections, and which offers a higher probability of the needle actually penetrating the skin rather than merely pushing the skin downwards without penetration or with only partial penetration, especially for needles with a relatively short length (e.g. shorter than 2.0 mm).

This and other objectives are accomplished by embodiments of the present invention.

In a first aspect, the present invention provides an assembly for forming an injection device for administering a fluid to a subject (in particular to a person), the assembly comprising: a foot part having a first contact surface adapted to be placed on a skin of the subject, the foot having a tubular shape for receiving a body; the body comprising at least one needle fixedly mounted to the body, and comprising a channel in fluid communication with the at least one needle for delivering the fluid to be administered to the subject, the body being movably mounted to the foot for allowing movement of the body from a first position in which the needle is in a retracted position not extending out of a first contact surface, to a second position in which the needle extends out of a second contact surface by a predefined distance for limiting a penetration depth of the needle; the assembly further comprising first friction means for inhibiting movement of the body relative to the foot when the body is in the first position, until a predefined static friction force is overcome, and for causing or allowing a sudden acceleration of the body towards the foot for increasing a speed of the needle for increasing the chance of penetration; the assembly further comprising second friction means for creating a dynamic friction between the foot and the body when the body is moving towards the foot for maintaining contact with the skin, the predefined dynamic friction being smaller than the predefined static friction.

It is an advantage of embodiments of the present invention that an assembly and an injection device comprising same are provided, which allow a fluid to be administered by a single hand, and thus is suitable for self-administration.

It is an advantage of at least some embodiments of the present invention that existing syringe-needle solutions for drug administering can be integrated with a means for automatic injection.

It is also an advantage of embodiments of the present invention that an assembly is provided which is less complex, and thus easier to produce.

With "fluid" is meant any matter which can be injected through a needle, such as for example a liquid, a suspension, a gel, or other substances which can be injected via a needle.

It is an advantage that this embodiment can be made with a single needle, or with a plurality of needles.

It is an advantage of the second contact surface that it helps ensuring a well-defined penetration depth of the needle tip(s) into the skin.

It is an advantage of an assembly according to embodiments of the present invention, that it can be used to build an injection device for administering certain drugs or vaccines, for example as a kind of "fast prototype" or to reduce cost of clinical studies by the fact that de device can be seen as an "add on" for existing and approved syringe devices.

The device is especially suitable for providing injections under a very precise angle and/or penetration depth, such as for example for ID-injections (Intradermal) with the needle(s) being oriented nearly perpendicular to the skin and being inserted typically to a very precise and predefined depth of for example about 1.0 mm with a tolerance of +/−0.10 mm or +/−0.05 mm, or even smaller, but other specific angles can also be used. But the present invention is not limited to ID-injections, and can also be used for IV (intravenous) or SC (subcutaneous) intramuscular injections, although in these cases the needle(s) would typically have a much larger length, for example at least 10 mm or at least 20 mm. The angle and/or penetration depth and/or the positioning of the device may be chosen differently for such types of injections.

It is a major advantage of the assembly according to embodiments of the present invention that it allows self-administration of a drug, in the sense that it requires only a single hand to administer the drug, for example in the following manner: After (i) optional addition of a standard syringe to the assembly, and (ii) optional unlocking of the device, the step of administration may comprise: 1) holding the assembly with one hand (e.g. between the thumb and the middle finger), 2) gently placing the assembly on the skin, and 3) pushing the assembly to the skin until the first friction force is overcome, thereby inserting the needle(s) in the skin with almost 100% probability of penetration, and with a highly accurate predefined penetration depth, and then 4) activation of a plunger (e.g. with the forefinger or index finger) to deliver the fluid, e.g. drug or gel or other substance through the needle(s) into the skin.

It is a major advantage of an assembly according to embodiments of the present invention that it requires only minimal skill and experience to correctly administer a fluid, in contrast to for example the manner in which Intradermal (ID)-injections are administered today.

It is a major advantage of this assembly that the risk of non-penetration or incomplete penetration (to the predefined penetration depth) of the needle(s) in the skin, is drastically reduced or almost completely eliminated. Also the risk of inserting the needle too deep is eliminated. Stated in other words, if the assembly is properly used, it is almost guaranteed that the skin will be penetrated, and that the needle tip(s) will be located at a predefined depth.

It is a major advantage of this assembly that the penetration depth of the needle(s) is highly controllable, and independent of the experience of the person using the assembly, and that the risk of incomplete penetration is drastically reduced or even eliminated. In case of needle depths smaller than a predefined value, this may also help to reduce the pain experienced by the subject, and/or to improve the therapeutic effect of the drug administration.

It is an advantage of the assembly that no spring is required for inserting the needle, and no internal or external mechanism for compressing, holding, and releasing such spring, but instead, with the assembly of the present invention, a force/pressure/potential energy and/or kinetic energy is built up in/provided by the hand and/or forearm and/or fingers of the person holding the assembly, yet the device contains a mechanism (by means of the static and dynamic friction force) that enables or disables this (external) force to have an effect. It is noted however that a spring may be used in an injection device using this assembly, for example to actuate a plunger, but this is unrelated to the insertion of the needle in the skin.

It is an advantage of the first friction means, which sets or defines the force/pressure/potential energy to be build-up before the needle(s) starts to move, can be well defined in a passive manner, e.g. by a clamping force between portions of the body part (also referred to herein as "body") and the foot (as will be explained further).

It is an advantage of the "dynamic friction" (also known as "kinetic friction" or "sliding friction") that it keeps the skin stretched or tensioned also after the static friction is overcome, while the needle(s) is/are moving towards the skin. It is an advantage that the value of the dynamic friction can be well defined in a passive manner, and that the value is smaller than the static friction force. This will cause the needle(s) to suddenly accelerate when the static friction force is overcome, so that the needle(s) will penetrate the skin with a relatively high speed (e.g. between 2 m/s and 15 m/s, or any other suitable speed), while the skin is stretched.

The optimum penetration speed, and thus the optimum first and second friction may be chosen differently for different needles (e.g. different number of needles, different diameter, different length, different angles, different needle-wall-thickness, different angle of the needle tip, etc.), and different customized assemblies (e.g. having different surface characteristics of the grooves and/or of the protrusions) can be made having different needles.

It is an advantage that the behaviour of such an assembly (or injection device comprising such an assembly) is predefined to function accurate and with high predictability.

It is an advantage that dynamic friction is used to transfer force exerted by the operator partially to the foot pressing the device onto the skin, because without the dynamic friction, the foot would press less against the skin once the static friction is overcome, and the skin would be less stretched, or the foot may even loose contact with the skin. However, because of the dynamic friction, a portion of the force exerted upon the assembly by the user will be transferred to overcome the dynamic friction, and this force keeps the foot pressed against the skin, and this keeps the skin stretched. The remaining portion of the force is mainly used to accelerate the needle(s), so that the needle(s) has/have a certain speed before coming into contact with the skin.

It is also an advantage that only a single body with a single tubular shape is required, and not multiple (as used in some prior art devices). This reduces the material cost, simplifies the design of the assembly, and simplifies the use of the assembly.

It is an advantage of the assembly that it provides a decoupling of the steps of: (a) positioning the device on the skin which can be slow, (b) actually inserting the needle(s) in the skin, which is rapid, and (c) the step of administration of the fluid (e.g. drug or vaccine or gel, etc.), which may be slow. The assembly allows step (b) to be kind of "automated" or "controlled", such that it can be applied faster, more accurate and requiring less skill. And there can even be a delay between these steps. Step (c) may be performed manually (e.g. moving a plunger with a finger), or may be partly or fully automated (e.g. using a spring). It is an advantage that the movement of step (b) is relatively well defined or controlled by means of the friction forces. The user only has to perform a simple action: placing the device on the skin and pushing sufficiently hard to overcome the static friction, and the rest goes automatically, without the user even having to think about it.

It is an advantage of an assembly according to embodiments of the present invention that it allows clinical trials to be conducted with reduced costs, since the assembly can be seen as a safe extension of (an) existing syringe-needle(s).

It is an advantage that the assembly of the present invention, and an injection device using this assembly, can be used as an injection research tool. Indeed, the concept and design are modular in the sense that it can be customized or fine-tuned for different types of needles (e.g. single needle versus multiple needles, and for different needle lengths, and for different needle diameters and for different needle materials. It is an advantage that only during later stages of the production, (namely when a needle is to be fixed to the body), a specific type of needle or needle array, with a specific length, is to be chosen, but that earlier production stages, e.g. where the body and the foot are formed by using injection moulding techniques, can be identical for different designs (e.g. having a different needle length). Hence customization is only required at the later stages in the process of manufacturing the components of the assembly.

It is an advantage that a large variety of existing needles, (but also needles still to be developed), can be mounted to the body. In this way, different assemblies can be produced for different applications, for example for administering different drugs, or for different groups of patients, each with the most suitable needle(s) available.

It is also an advantage that a needle array, chosen from a wide variety of configurations, can be attached to the body during its production.

Preferably the static friction force is at least 2.0 Newton, and the dynamic friction is at least 1.0 Newton. This means that a weight of about 200 grams would be sufficient to overcome the static friction, and that a force equivalent to a weight of at least 100 grams thereof is used to keep the assembly pushing against the skin during movement of the needle, due to the dynamic friction.

In an embodiment, an angle between a longitudinal axis of the at least one needle and a tangential plane defined by the first contact surface(s) is a value in the range of 5° to 175°, for example from 10° to 170°, for example from 60° to 120°, for example from 80° to 100°, e.g. about 90°.

It is an advantage of such an embodiment that it allows to administer Intradermal injections under a predefined angle.

It is a particular advantage of such an assembly that it can be used to administer ID-injections (intradermal) under an angle in the range from 60° to 120°, which is completely different from the so-called "Mantoux-technique", which is reported to be a painful method from patient's perspective of administering ID drugs under an angle of about 10° to about 15° for forming a "bleb" just underneath the skin. Inserting the needle(s) under an angle close to 90° is expected to be a lot less painful, and probably also provides a medical advantage because the injected fluid may spread better between the cells.

In an embodiment, the second contact surface has a disk shape or a dome shape, the at least one needle preferably being positioned in the centre of said disk shape or at the top of the dome shape.

If a (planar) disk shape is used, it preferably has a bevelled or a rounded rim, but that is not absolutely required. The dome-shape can be any 3D-rounded surface, for example a hemi-spherical shape or a parabolic shape, or the like. Such surfaces all offer the function of precisely defining the penetration depth, without injuring the skin at the periphery of the second contact surface, despite the acceleration.

In an embodiment, the predefined static friction force is a value in the range from 0.5 to 50 Newton, e.g. from 1.0 to 20.0 Newton; and a ratio R=FD/FS of the predefined dynamic friction force and the predefined static friction force is a value in the range from 10% to 90%.

The predefined static friction force can for example be a value in the range from 1.0 to 20.0 Newton, or from 1.5 to 15 Newton, or from 2.0 to 10 Newton, or from 5.0 to 7.5 Newton. Such a force does not require too much effort from the person handling or using the assembly, and can readily be applied by all envisioned users and personnel, young and old. The force need not be very large, because the force/energy required to penetrate the envisioned needles is typically quite small. This also has a psychological effect, in that the subject does not experience a sudden vibration, only a gentle puncture. It may feel like "pushing a button, and before you realize it, the needle(s) is/are inserted into the skin".

The ratio of the dynamic friction and the static friction R=FD/FS is defined by the physical shape and/or dimensions of the assembly, in particular e.g. the radial dimensions of protrusions and grooves, and/or surface finishing of the protrusions and grooves, and/or material characteristics, etc. This ratio R=FD/FS can be a value in the range from 20% to 80%, or from 30% to 70%, or from 40% to 60%, or from 10% to 30%, or from 20% to 40%, or from 30% to 50%, or from 40% to 60%, or from 50% to 70%, or from 60% to 80%, or from 70% to 90%. The optimal ratio may be chosen differently for different groups of people (e.g. depending on age and/or gender), or may be chosen differently for different location of administration (e.g. upper leg, upper arm, etc.). In case the value of the "predefined dynamic friction force" is not exactly constant during the movement (which is indeed not required), the ratio can be calculated as the ratio of the average dynamic friction value and the predefined static friction.

In an embodiment, the first friction means comprises at least two protrusions (e.g. one or two sets of two or three protrusions each) extending from an outer surface of the body being in contact with at least two corresponding grooves located on an inner surface of the foot, wherein a radial dimension (e.g. radius or diameter) defined by the at least two protrusions before assembly of the body and the foot, is larger than a corresponding radial dimension (e.g. radius or diameter) defined by the grooves, the static friction being provided by radial clamping of the protrusions and the grooves.

In an embodiment, the first friction means comprises at least two protrusions (e.g. one or two sets of two or three protrusions each) extending from an inner surface of the foot being in contact with at least two corresponding grooves located on an outer surface of the body, wherein a radial dimension (e.g. radius or diameter) defined by the at least two protrusions before assembly of the body and the foot, is smaller than a radial dimension (e.g. radius or diameter) defined by the grooves, the static friction being provided by radial clamping of the protrusions and the grooves.

In these embodiments, the friction force is defined by a radial clamping force, and its magnitude is primarily defined by radial dimensions.

It is an advantage that the parts of the present invention can be implemented for example by near-shape manufacturing technologies, like precision casting, additive manufacturing, 3D-printing, injection moulding of plastics material, etc., and that the tolerances of such a process can be precisely controlled, for example in the order of 0.01 mm or 0.02 mm or 0.03 mm. This allows to implement the friction forces with high accuracy.

It is an advantage of using protrusions and grooves for defining the static and dynamic friction force, because it allows to easily adapt the friction force, and their ratio, by merely changing the dimensions (radial, height and width) of the protrusions and/or the radial dimensions of the grooves.

In an embodiment, the assembly comprises a single needle, and the grooves are at least partly spiral grooves, for rotating the needle when the body is moving towards the foot.

It is an advantage of embodiments wherein grooves with a spiral portion are used in that they provide rotation to the needle, in addition to the axial acceleration. This may further decrease the risk of non-penetration or incomplete penetration of the needle, at least for some needle-designs, and may further reduce the risk of merely pushing the skin downwards without actually penetrating the skin.

Stated in other words, controlled rotation of the needle may allow a larger range of needles to be used, or may allow new/different needle materials to be applied, or may allow needles with different sharpness, different distal profile, different surfaces, different angles, and/or needle tips with different cuts, different profiles, different geometries, surfaces, tapered needles, needles with optimized flow, etc. to be used. This may be especially advantageous for small penetration depths, and thus for ID-injections. Rotation of the needle, even over a relatively small angle, such as only about 5° or only about 10° may help to further increase the probability of complete penetration of the needle.

In an embodiment, the body further comprises a cavity in fluid communication with the at least one needle, the cavity being adapted for receiving and accommodating a syringe, the syringe comprising the fluid to be administered and further comprising a plunger movable inside the syringe for forcing the fluid out of the syringe.

This is a first kind of assembly, intended for cooperation with an external syringe. This offers the advantage that existing syringes can be used. The combination of an existing syringe and an assembly according to embodiments of the present invention combines the benefits of (inter alia): 1) guaranteed skin-penetration, 2) predefined penetration depth, 3) easy to handle, low skill and experience required, with the benefit of being able to use existing and medically approved syringes.

However, compared to pre-filled devices, these embodiments are an ideal tool for investigational needles, without having to produce an entire injection device for each of them.

This also offers the advantage that the assembly, or rather an injection device comprising such an assembly, can be used to administer any drug or vaccine, in a controlled manner. In that case, the assembly is part of a combinational injection system by utilizing existing syringes, needle(s) and drugs.

In an embodiment, the cavity has a conical channel with standard Luer dimensions for receiving the syringe.

For example, the assembly may have a female connector which is Luer compatible. This allows the use of any Luer compatible syringe, but of course, other suitable dimensions, or even a conical channel with multiple portions having different dimensions would also be possible.

In an embodiment, the body further comprises a cavity in fluid communication with the at least one needle, the cavity having a tubular shape suitable for containing the fluid to be administered, and suitable for receiving a plunger and for allowing axial movement of said plunger for forcing the fluid out of the cavity.

This is a second kind of assembly, intended to be pre-filled. Such an assembly thus has its own cavity (or chamber) acting as a reservoir for holding the fluid, e.g. a vaccine, drug, cosmetic gel, etc. An injection device using this assembly is referred to herein as a "pre-filled injection device". Such single-use devices may be better suited for mass-production, because of lower product costs (as compared to the assembly of the first kind, described above, where a separate syringe is to be inserted). The tubular shape may be a cylindrical shape, but tubular shapes with a non-circular cross-section can also be used (in combination with a corresponding plunger).

In an embodiment, the predefined distance by which the at least one needle extends out of the second contact surface is a distance in the range of 0.25 to 12.0 mm, or from 0.25 to 5.00 mm, or from 0.25 to 2.00 mm.

A distance from 5.0 mm to 12.0 mm, for example from 10 mm to 120 mm may be especially suitable for IM injections. A distance from 0.25 mm to 8.00 mm, for example from 1.00 mm to 5.00 mm may be especially suitable for SC injections. A distance from 0.25 mm to 3.00 mm may be especially suitable for ID injections.

In an embodiment, the body comprises a plurality of needles extending from said second surface, the number of needles being a value in the range from 2 to 49, for example 3 or 4 or 5 or 6 or 9 or 16 or 25 or 36.

The needles may be arranged in a regular pattern, such as e.g. on a one-dimensional line, or on a two-dimensional array, or on a circle, or on two or more concentric circles, or in an irregular pattern, or combinations hereof, or in any other suitable arrangement.

It is an advantage of an assembly with a plurality of needles, e.g. using a so called "microneedle array" that it combines the advantages of multiple needles with the "guaranteed penetration" and "accurate penetration depth" offered by the present invention. One such advantage is that the needles can be thinner, causing smaller wounds, and/or that a smaller amount of fluid can be administered at many different places, by a single action. Another advantage is that, because of the smaller needle diameter, the (sloping) needle tip can be smaller, and hence also the penetration depth can be smaller (for example about 0.4 or 0.5 or 0.6 mm). Using more than one needle can help to increase the flow rate and/or to decrease injection pressure.

In an embodiment, the assembly further comprises a locking mechanism for providing a locked mode and an unlocked mode of the device; the locked mode being a mode of the assembly, wherein the body is prevented from moving axially to the foot, even when an axial force larger than the predefined static friction is exerted on the body relative to the foot; the unlocked mode being a mode of the assembly wherein the body is allowed to move towards the foot, when an axial force larger than the predefined static friction is applied to the body relative to the foot.

In this embodiment, the assembly further contains a "locking mechanism" (also referred to herein as "activation mechanism"). It is an advantage of the locking mechanism that the risk of inadvertently bringing the needle(s) to its/their distal position before the foot is placed on a skin (e.g. during preparation of the "injection device" using said assembly) is reduced, e.g. minimized until the last step prior to injection.

Different ways to implement the locking mechanism can be provided. In a preferred embodiment, the locking mechanism is implemented mechanically by grooves having a zig-zag-shape or double-L-shape, the zig-zag-shape having a first, axial portion for receiving protrusions during assembly of the body inside the foot, resulting in an assembly in the "locked state". The zig-zag-shape further comprising a second, circumferential portion for allowing the assembly to be unlocked when the foot is rotated relative to the body around the longitudinal axis, resulting in an assembly in the "unlocked state". The zig-zag-shape further comprising a third, axial or spiral portion for guiding the protrusions when the body is moved towards the foot with/without additional rotation of the needle, when the static friction force is overcome.

In an embodiment, the foot is at least partly deformable to such an extent that an outer dimension of the first contact surface is capable of increasing by at least 3%, when the foot is being pressed against the skin with a force equal to the predefined static friction.

The foot may be flexible and/or elastic.

The outer dimension (e.g. the diameter of the smallest possible imaginary circle around the contact surface) may be capable of increasing at least 5%, or at least 8%, or at least 10%, or at least 15%, or even more, for example at least 20% or even at least 30%, when applying a force substantially equal to the static friction force, in axial direction.

This may for example be implemented by using suitable materials, e.g. flexible materials and/or elastic materials. In an embodiment, the foot or part of the foot comprises or is made of a material having a shore in the range from 10 to 70, for example in the range from 20 to 60, for example in the range from 30 to 50.

This may for example be implemented by using a suitable structure and/or shape and/or texture and/or surface finishing. In the same or a further embodiment, the foot or part of the foot is shaped such that the foot has a plurality of "segments or flaps or wings" with cut-outs in between, each segment or flap or wing optionally further comprising a zone, e.g. circumferential groove with a thinned thickness.

In particular embodiments, both a flexible material and a flexible structure may be used.

It is an advantage of using a flexible or bendable foot because such a foot at least partly converts an axial force exerted by the user on the body when the body is placed on the skin, and e.g. oriented substantially perpendicular to the skin into a radially outward directed force (e.g. shear force) stretching or tensioning the skin. This may further increase the probability of guaranteed penetration, and/or the probability of complete penetration to the predefined penetration depth. Stretching the skin will typically also reduce the thickness of the "bulge" (i.e. upwardly bended skin inside the region defined by the foot) created when placing the foot on the skin, so as to create an improved, e.g. ideal condition of the skin for receiving the needle(s).

It is an advantage of the flexible or bendable foot that it allows the skin to be stretched without requiring a second hand, in contrast to the prior art where medical personnel would typically stretch the skin by moving the thumb and forefinger or index finger apart with a first hand, while inserting the needle(s) with a second hand. The assembly of the present invention allows to stretch the skin by simply pushing the body towards the skin, in the same action as inserting the needle(s), thus requiring only a single hand.

As far as is known to the inventors, the skin is commonly stretched in the prior art either manually by spreading fingers of a second hand, or by placing a closed curve such as a circular foot on a skin, but after the foot is placed on the skin, it is not further stretched, whereas in the present invention, the skin is further stretched after the foot is placed on the skin, even when using a single hand. And the dynamic friction force ensures that the skin remains stretched, decomposing the perpendicular force in inter alia a component parallel to the skin, even after the static friction force is overcome.

In a second aspect, the present invention provides an injection device comprising: an assembly according to the first aspect, in as far as it has a cavity with a cylindrical shape suitable for containing the fluid to be administered, and wherein said cavity further comprises the fluid to be administered, and wherein said cavity further comprising said plunger.

This embodiment provides a "pre-filled injection device" based on an assembly according to embodiments of the present invention.

In a third and fourth aspect, the present invention provides an injection device and a kit of parts comprising: an assembly according to the first aspect, in as far as it has a cavity for receiving a syringe; a syringe comprising a plunger, the syringe having an outer diameter smaller than the inner diameter of the cavity, the syringe optionally comprising the fluid to be administered; optionally a vial containing the fluid to be administered; optionally a removable needle or other means for extracting the fluid from the optional vial into the syringe, the needle being removable for allowing the syringe to be inserted in the cavity of the body of the assembly.

This provides an injection device and a kit of parts based on an assembly according to the first aspect, where the assembly is of the first kind, i.e. adapted to be used in conjunction with an existing syringe.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1(a) shows an exemplary assembly and an exemplary injection device according to embodiments of the present invention, in perspective view.

FIG. 1(b) to FIG. 1(d) show variants of the assembly and of the injection device of FIG. 1(a) according to embodiments of the present invention. The main difference between these embodiments and that of FIG. 1(a) is that the foot is flexible and/or bendable rather than stiff in FIG. 1(a).

FIG. 1(e) shows an exemplary embodiment of a pre-filled injection device according to embodiments of the present invention.

FIG. 2 shows an exemplary body as can be used in embodiments of the present invention.

FIG. 3 shows an exemplary foot as can be used in embodiments of the present invention.

FIG. 4 shows a cross-section of the injection device of FIG. 1(a) as seen from the position indicated by "IV" in FIG. 2.

FIG. 4(a) shows the device in a first state (also referred to herein as the "unlocked" state or "ready-to-insert-the-needle" state), wherein a first and a second protrusion of the body, extending left and right of the body in FIG. 4(a), are in contact with an inner surface (e.g. groove) of the foot.

FIG. 4(b) shows the device in a second state (also referred to herein as the "ready-to-inject-the-fluid" state), wherein the first and second protrusion are still in contact with the inner surface of the foot, but the body has been shifted towards the foot.

FIG. 5(a) is an enlarged view of a lower part of FIG. 4(a).

FIG. 5(b) is an enlarged view of a lower part of FIG. 4(b). Some internal structures like ribs and grooves are not shown for illustrative purposes.

FIG. 6 shows a cross-section of the injection device of FIG. 1(a) as seen from the position indicated by "VI" in FIG. 2, perpendicular to the viewing position indicated by "IV" in FIG. 2.

FIG. 6(a) shows the device in the first state, wherein a third and fourth protrusion of the body, extending left and right of the body in FIG. 6(a), are in contact with an inner (upper) surface of the foot.

FIG. 6(b) shows the device in the second state, wherein the third and fourth protrusion of the body are no longer in contact with an inner surface of the foot.

FIG. 8(b) shows a typical graph of the combined friction force provided by the protrusions shown in FIG. 2, versus time.

FIG. 9 is also used to illustrate (in the same drawing) how the material of the flexible or bendable foot bends outwardly and stretches the skin, which may further help to guarantee penetration of the skin, and may help to further control the penetration depth of the needle.

FIG. 11 shows the injection device of FIG. 10(b), having a cavity with a conical portion acting as a female connector adapted for receiving a syringe with a male protrusion, for example according to the "standard Luer interface". FIG. 11(a) shows such a device in cross section, with a prior art syringe and plunger inserted thereto. FIG. 11(b) shows the body of the device in cross section. FIG. 11(c) shows the body of the device from the outside (similar to FIG. 2). FIG. 11(d) shows the body of FIG. 11(c) as seen from viewing location "C" in FIG. 11(c).

FIG. 12(a) to FIG. 12(c) show a variant of the body shown in FIG. 11(b) to FIG. 11(d), not having a female connector for receiving a syringe, but instead having a cylindrical cavity forming a reservoir for holding a liquid to be injected. This body can be used to form a "prefilled device" according to an embodiment of the present invention.

Figures 7A, 7B:
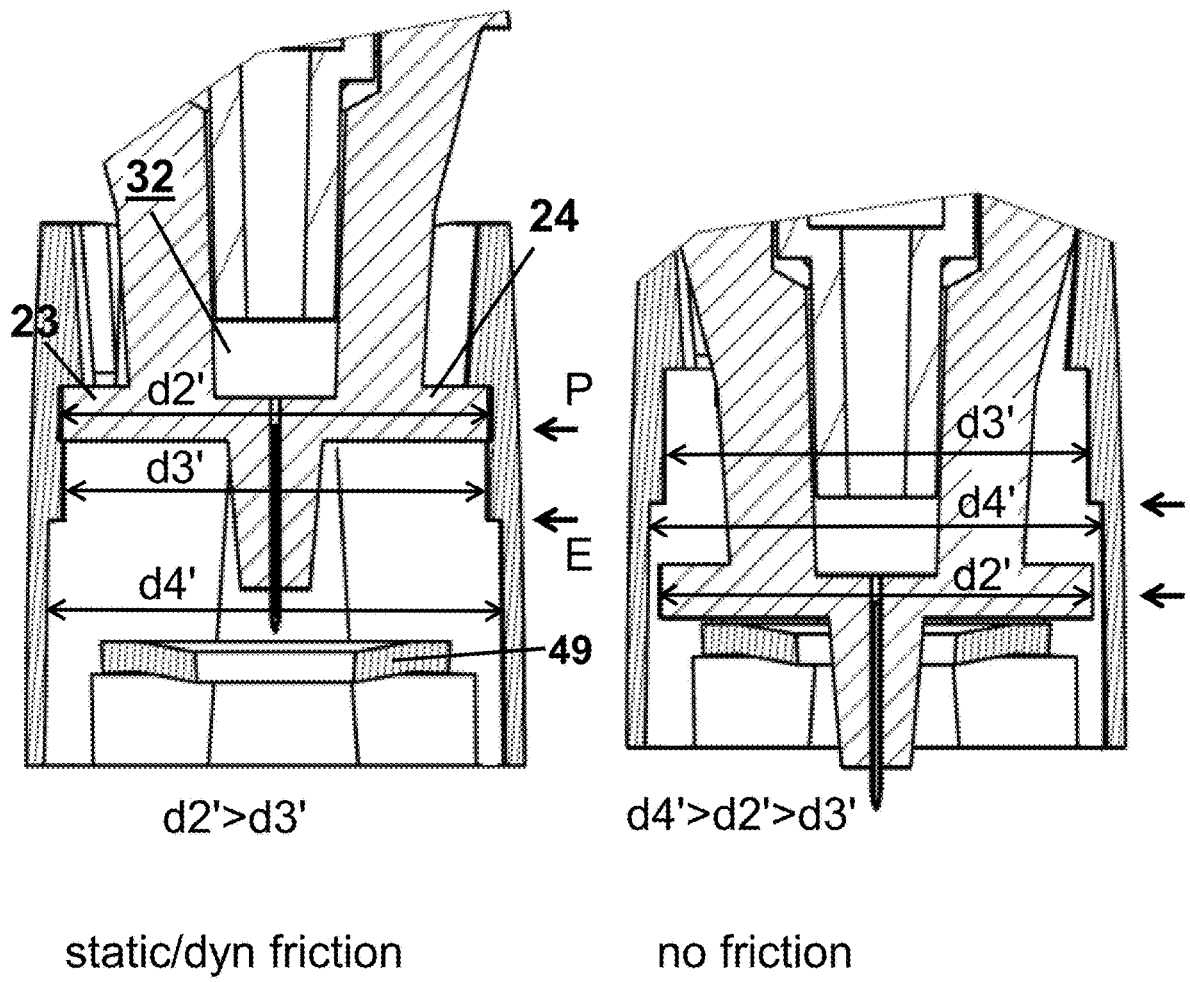
FIG. 7(a) is an enlarged view of a lower part of FIG. 6(a). Some internal structures like ribs and grooves are not shown for illustrative purposes.
FIG. 7(b) is an enlarged view of a lower part of FIG. 6(b). Some internal structures like ribs and grooves are not shown for illustrative purposes.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In this document, the terms "dynamic friction", "kinetic friction" or "sliding friction" are used as synonyms.

In this document, the terms "locking mechanism" and "unlocking mechanism" and "activation mechanism" are used as synonyms.

The inventors had the task of designing an injection device that offers a very high probability of effectively penetrating the skin to a predefined depth, and/or which is easier to produce, and/or the use of which allows to administer a fluid by a single hand, and preferably all of these, and came to the idea of developing a module, referred to herein as "assembly" which offers the required functionality, but does not necessarily have its own reservoir, and does not necessarily have a locking mechanism, and does not necessarily have a needle retraction mechanism.

The inventors learned from experiments that for small penetration depths (e.g. less than 2.0 mm), even when the skin is stretched by placing a rigid foot with a circular perimeter on the skin, it is a challenge to guarantee that the needle always penetrates the skin, and moreover penetrates the skin over the envisioned penetration depth. They found that, using classical devices, the skin is often merely punched by the needle and merely pushed downwards, rather than firmly punctured. They also found that increasing the force (without increasing the speed) does not necessarily help to guarantee good penetration, but a combination of a stretched skin and sufficient energy or momentum or speed does guarantee proper insertion of the needle in the skin.

In order to increase the probability of penetration, they came to the idea of using a combination of acceleration based on static friction and dynamic friction, in such a way that, during use, (when the assembly is placed on the skin, and the needle tip is still located inside the body), a force or pressure or potential energy is first to be built up in a user's forearm and/or hand and/or fingers until a predefined static friction force is overcome, at which point the needle will start to move relative to the foot, and will accelerate toward the skin, so as to contact the skin at relatively high velocity, in a manner not requiring a spring. In addition, in order for the device to keep the skin stretched and in order not to lose contact with the skin during said acceleration of the needle, they decided to make sure that part of the energy or force provided by the user's finger/hand/forearm is used to continue pushing the device against the skin by means of a dynamic friction force, while the body and the needle is moving. In this way the skin remains stretched, even during said acceleration. This is one of the underlying ideas of the present invention.

This principle is believed to be non-obvious, inter alia because it is counter-intuitive to use "friction" for accelerating a needle, because friction is typically used to slow-down objects.

The invention will now be further elucidated with reference to specific embodiments, but the present invention is not limited to these detailed examples, but to the subject matter as defined by the claims.

FIG. 1(a) shows an exemplary embodiment of an assembly 101, and of an injection device 151 comprising such an assembly, in perspective view. The injection device 151 comprises an assembly 101 (lower part of FIG. 1a) and a prior art syringe 50 with a prior art plunger 51. The interconnection between the syringe 50 and the assembly 101 may be based on a male and female interconnection as will be described in FIG. 11(a). The connections may be Luer compatible, but another, e.g. proprietary interface may also be used.

The assembly 101 comprises two main components: a "body part" 20 (also referred to herein simply as "body") and a "foot part" 40 (also referred to herein as "foot"). An example of the body 20 will be described in more detail in FIG. 2. An example of the foot 40 will be described in more detail in FIG. 3.

As illustrated in FIG. 1(a), the body preferably has gripping means 25 on an outside surface, at opposite sides of the body 20 (only one gripping means is visible in FIG. 1, both are visible in FIG. 2) for allowing the device to be held firmly for example between a thumb on one side, and a middle finger and/or ring finger on the opposite side, or by the palm of the hand on one side and four fingertips on the other side, or in any other suitable way. This allows easy placement of the device (in particular the foot thereof) on a skin, and allows the body 20 to be pushed toward the skin for inserting the needle in the skin, as will be described in more detail further, when discussing FIG. 4 to FIG. 9.

For completeness, it is noted that the forefinger or index finger (in the first example) or the thumb (in the second example) would typically be used only later, after the needle is inserted in the skin, for actually forcing a fluid out of the syringe 50, by pressing the plunger 51, and that the fluid would typically be introduced in the syringe 50 during a preparation step using for example the classical method of placing a metal needle on top of the syringe 50, introducing the needle in a container or vial, and pulling the plunger 51 for extracting fluid from the container or vial. However, instead of manually inserting the needle of the syringe 50 in a skin (as is done in the prior art), in order to use the assembly of the present invention, the needle would be removed from the syringe 50, and the syringe 50 would be connected to the body 20 of the assembly 101 (see also FIG. 11(a)), and after pushing the assembly towards the skin, the needle 28 of the assembly 101 will penetrate the skin.

If the assembly 101 comprises an optional locking/unlocking mechanism (also referred to as "activation mechanism"), the foot 40 would for example have to be rotated first over about 30° about its longitudinal axis relative to the body 20 before the body 20 can move toward the foot. This may help to reduce the risk of inadvertently moving the body relative to the foot until the moment of actual administration of the fluid. In this way the risk of inadvertently touching the needle before administration of the fluid is reduced, e.g. minimized. After the syringe 50 is connected to the body 20, the foot 40 would then be rotated around the longitudinal axis of the device, in order to "unlock" the device, and the device would be placed on a skin 90, as described above (see also FIG. 9).

Of course, it is also possible to hold the assembly in a fist, by surrounding it with for example with four fingers, while orienting the thumb upwards. After pushing the body towards the skin with a sufficiently large force, and after the needle 28 has penetrated the skin 90, the plunger can then be pushed using the thumb.

In contrast to many prior art devices, only a single hand is required for holding and pressing the injection device against a skin, and for administering the fluid. But of course, a person may also use both hands, for example one hand to move the body 20 towards the foot 40, and the other hand to push the plunger.

FIG. 1(b) to FIG. 1(d) show variants of the assembly 101 and of the injection devices 151 shown in FIG. 1(a). The main difference between these embodiments and that of FIG. 1(a) is that the foot 40 is flexible and/or bendable, whereas in FIG. 1(a) the foot is rigid.

In FIG. 1(b) the foot 40 has a planar circular rim 45 or 35 as in FIG. 4, and a lower portion of the foot has a substantially conical shape, the rim 45 being directed outward.

In FIG. 1(c) a lower portion of the foot 40 has a shape comprising two flaps or two wings 47 and two cut-outs 46 between the flaps or wings, but of course, more than two flaps or wings 47 would also be possible, for example three, four, five, six, or more than six flaps or wings. In the embodiments shown in FIG. 1(c) and FIG. 1(d) the cut-outs 46 have a rounded shape, but that is not absolutely required for the present invention to work.

In FIG. 1(d) a lower portion of the foot 40 has four flaps or wings 47 defined by four cut-outs 46.

The entire foot may be flexible or bendable, or only a portion thereof. The main benefit of the flexible or bendable foot or foot portion is that it allows to stretch the skin, or to further stretch the skin, when pushing the body 20 towards the skin 90. Indeed, as explained above, due to the dynamic friction, a significant fraction (e.g. at least 10%) of the force exerted on the body 20 will be used to bend the flaps or wings 47, which will cause the skin 90 to stretch.

In case of multiple needles (see further), the position of the flaps or wings 47 may be aligned with the needles. For example, in case three needles are used, the flaps may be oriented to stretch the skin in the direction parallel to a virtual line through the three needles, or may be oriented to stretch the skin in a direction perpendicular to said virtual line.

The skilled person can easily find a suitable shape of the flaps or wings 47 for providing a suitable flexibility. The flexible or bendable foot or foot portion can be produced in any known manner. For example, if the foot is produced as a single piece, the flexible portion can be produced by co-injection, for example by using a relatively rigid material (on top) and a relatively soft material for the flaps. If the foot is produced as two pieces, a rigid upper part can be produced (as shown in FIG. 3), and a bendable part, e.g. ring-shaped can be added to the rigid part, for example by means of a circular protrusion fitting in a circumferential groove, or vice versa. The foot or part of the foot can for example comprise or can be made of a material having a shore in the range from 20 to 60, for example in the range from 30 to 50, but other values may also be used. Stretching the skin in this way may further help to improve the chance of guaranteed penetration, and in case of multiple needles, it may help to more evenly spread the points of actual penetration.

FIG. 1(e) shows another embodiment of an assembly 201, and an injection device 251 comprising said assembly 201. The main difference between this embodiment and that of FIG. 1(a) to FIG. 1(d) is that it does not have a female connection for receiving a standard syringe, but it has its own reservoir, adapted for receiving a plunger. But apart from this difference (at the side of the body facing away from the skin), everything else is also applicable for this embodiments. For example, this assembly 201 can also comprise a foot end like the ones shown in FIG. 1(b) to FIG. 1(d). In fact, FIG. 9 shows such an injection device in cross section.

FIG. 2 shows an exemplary body 20 as can be used in embodiments of the assemblies 101, 102, 103, 104, 201 and the injection devices 151, 152, 153, 154, 251 shown in FIG. 1, in perspective view.

Actually the present invention provides two kinds of bodies, one kind (indicated with reference 20) shown inter alia in FIG. 2, FIG. 11 and FIG. 13 has a cavity 27 for receiving an existing syringe, the other kind (indicated with reference 60) shown inter alia in FIG. 9, FIG. 12 and FIG. 14, has a cylindrical cavity 67 acting itself as the reservoir for holding the fluid to be injected and for receiving a plunger 66. In the latter case, any existing seal and/or plunger 66 can be used.

Injection devices based on the first kind of assembly 20 are referred to herein as "combi-devices". Injection devices based on the second kind of assembly 60 are referred to herein as "pre-filled devices".

Apart from this difference, everything mentioned for the body with reference 20 is also applicable for the body with reference 60, and vice versa, unless specifically mentioned otherwise.

Referring back to FIG. 2, as can be seen, the body 20 preferably has gripping means 25a, 25b located on opposite sides of the body, for allowing easy grip of the body in a single hand. The gripping means 25a, 25b shown are based on a rim, but other gripping means, for example providing a non-planar surface for easy placement of fingers, or any other suitable shape may also be provided.

The body 20 further comprises means 21-24 for providing static friction between the body 20 and the foot 40, and means 21-24 for providing dynamic friction between the body 20 and the foot 40, at least during part of the movement of the needle, when the needle is moving from a retracted position to an extended position. In the specific embodiment shown, the means for providing static friction comprise a first set of protrusions 21,22 and a second set of protrusions 23-24 adapted for being received and moved in a corresponding first and second set of grooves 41-42, 43-44 provided in the foot 40. In an alternative embodiment (not shown), the foot may comprise protrusions extending inwardly, and the body main comprise corresponding grooves. In the specific embodiment shown in FIG. 2, each set of protrusions 21,22 and 23-24 consists of exactly two protrusions extending radially outwardly from the body 20 on opposite sides thereof, but one or two sets of two or three protrusions could also be used, or one set with two, and one set with three protrusions.

How these protrusions interact with the grooves 41-44 of the foot 40 will be explained in relation to FIG. 4 to FIG. 7, and the resulting effect will be described in FIG. 8.

FIG. 3 shows an exemplary foot 40 as can be used in conjunction with the body 20 shown in FIG. 2. An alternative embodiment of the foot (not shown) may have protrusions extending radially inwards for engaging a plurality of corresponding grooves of the body (not shown), but the working principles would remain the same.

The grooves 41-44 in the foot may be oriented axially (e.g. in case no locking mechanism is provided), or may have a zig-zag portion (as shown). If present, the zig-zag portion could be used to provide a locking/unlocking mechanism to prevent accidental axial movement of the body 20 relatively to the foot 40 (e.g. when mounting the syringe 50 to the body 20), until after the foot 40 is rotated around the longitudinal axis of the body.

In FIG. 3 the lower portion of the grooves are oriented axially, but they could also define another downward route, for example a spiral route, for additionally providing rotation to the needle 28 as the needle moves toward the skin. Such rotation may further improve the probability of penetration, and may further improve the accuracy of the penetration depth of the needle in the skin.

The assembly 101 can be formed by producing the body and the foot, positioning the body 20 and the foot coaxially, orienting the body 20 and/or the foot 40 such that the protrusions 21-24 are aligned with the corresponding grooves 41-44, and pushing the body 20 towards the foot 40 thereby inserting the protrusions 21-24 in the grooves 41-44 to a predefined depth. If the locking mechanism is present, the protrusions can be pushed until they reach a surface or ridge, such as for example the surface 92 shown in FIG. 3.

FIG. 4 shows a cross-section of the injection device 151 of FIG. 1(*a*) as seen from the position indicated by "IV" in FIG. 2, comprising a body 20 and a foot 40 forming the assembly" 101, and further comprising a syringe 50 including a plunger 51. As can be seen, the syringe 50 is inserted in a cavity 27 of the body 20, and is held by a plurality of ribs 26. Although the ribs are not absolutely required, they may help easy insertion of the syringe 50 in the cavity 27, and cope with tolerance differences between the outer diameter of the syringe 50 and an inner diameter of the cavity 27, and may help to provide a stable positioning of the syringe. The ribs may also act as guides in order to prevent the male protrusion 56 (see FIG. 11(*a*)) from hitting the side walls of the cavity 27, which may improve sterility.

The syringe 50 has an inner space 54, acting as reservoir for holding the fluid (not shown) to be administered. The syringe 50 typically further comprises a plunger 51 for pressing the fluid out of the syringe. The plunger 51 typically comprises a sealing element, e.g. a rubber element 53.

The syringe 50 may have a conical tubular portion 56 (see FIG. 11(*a*)), acting as a male connector element, which may be compatible to the Luer-standard, but that is not absolutely required for the present invention to work, and other interfaces, for example proprietary interfaces may also be used. The male connector portion 56 engages with a female conical connector portion 31 (see FIG. 11(*a*)) of the body 20. More relevant for the present invention, however, are the protrusions 21,22 and the corresponding grooves 41, 42 accommodating them.

FIG. 4(*a*) shows the injection device 151 in a first state (also referred to herein as "unlocked state" or "ready-to-insert-the-needle" state), wherein a first and second protrusion 21, 22 of the body 20, visible on the left and right side of the body 20 in FIG. 4(*a*), are in contact with an inner surface, e.g. inner groove 41, 42 of the foot 40. The body 20 is at a distal position relative to the foot 40. The needle 28 is fixedly mounted to the main body 20, and is not accessible from the outside of the assembly, hence the risk of accidental needle puncture is minimal.

FIG. 4(*b*) shows the assembly 101 after the body 20 of FIG. 4(*a*) is pushed over distance "d1" towards the foot 40. The device is in a second state (also referred to herein as the "ready-to-inject-the-fluid" state), wherein the first and second protrusion 21, 22 are still in contact with the inner surface, e.g. inner grooves 41, 42 of the foot 40. The body is at a proximal position to the foot.

Although not visible in FIG. 2, the needle is accurately positioned and fixed in the body 20 during the manufacture of the body, in a manner so as to extend with a predefined distance "p2" outside of a "reference surface", a second contact surface 30, also referred to herein as "contact surface" 30. This can for example be accomplished by automatic positioning of the needle or needles in an opening of the body 20 using a robotic arm, and performing the fixation by gluing or by melting or partially melting material, or in any other way.

The "reference surface" 30 moves along with the body 20 and with the needle 28, and will come in contact with the skin in order to define a precise penetration depth equal to the distance "p2". In the example shown in FIG. 4(*b*), the contact surface 30 itself extends by a predefined distance "e1" outside of the plane 91 defined as a virtual plane tangential to the foot, but that is not absolutely required for the invention to work, and the distance "e1" may also be a slightly negative value (i.e. located higher than the reference surface 91), because as illustrated in FIG. 9, the skin will typically form a small bulge directed upwards. Although the value of "e1" is not critical for the present invention, it is preferably at least zero or a positive value. As can be appreciated from FIG. 4(*b*) the distance "e1" is defined by the relative dimensions and relative position of the stop surface 49 (part of the foot) and the length of the needle holder 29 surrounding the needle. Thus the stop surface 49 has two functions: (i) to stop movement of the body, and (ii) to prevent accidental access to the needle when the needle is still in a retracted position (before the static friction force is overcome).

FIG. 5(*a*) is an enlarged view of a lower part of FIG. 4(*a*), and FIG. 5(*b*) is an enlarged view of a lower part of FIG. 4(*b*), where some internal structures like ribs and grooves are not shown for illustrative purposes. These drawings allow to appreciate how the static friction and dynamic friction provided by the protrusions 21, 22 work, namely, by providing a body 20 and a foot 40 having dimensions such that, before assembly, an outer radial dimension "d2" defined by the protrusions 21, 22 is larger than an inner radial dimension "d3" defined by the corresponding grooves 41, 42, for causing a radial clamping force after assembly of the body 20 and the foot 40, or in case a locking mechanism is provided, after rotating the foot 40 relative to the body 20.

In case the body 20 has two protrusions 21, 22, the outer radial distance can be an outer diameter (as shown in FIG. 5(*a*)). In a variant wherein the body has for example three or more protrusions, e.g. spaced apart over 120° or 90°, the outer radial distance can be defined as twice a radius from the axis of the body to the outer radial position of the protrusions. In a variant wherein the foot has protrusions, and the body has grooves, the outer dimension defined by the grooves would be larger than the inner dimensions defined by the protrusions, again to provide a clamping force between them.

Instead of radial pressure, the friction could also be provided by a slightly larger thickness (e.g. diameter) of the protruding pens (e.g. having a cylindrical shape), being forced in grooves having a slightly smaller width (measured in circumferential direction).

The radial clamping force provides a static friction between the body 20 and the foot 40, which static friction needs to be overcome before the body 20 can move relative to the foot 40 and thus before the needle can move towards the skin (during actual use). At the moment at which the static friction is overcome, the body 20 including the needle 28 will suddenly accelerate toward the skin.

However, preferably the body 20 is not simply released in an uncontrolled manner, but instead, the acceleration is still controlled by a dynamic friction between the moving protrusions 21, 22 and the grooves 41, 42. It is a deliberate choice of the inventors to provide grooves 41, 42 having an inner dimension "d3" smaller than the dimension "d2" defined by the protrusions, for creating a non-zero dynamic friction between the body 20 and the foot 40 when the body moves towards the foot, for example during at least 40% or at least 50% or at least 60% or at least 70% or at least 80% and preferably during 100% of the travel distance "d1". In this way, part of the force exerted by the user on the body 20 will be transferred to the foot 40 for maintaining at least part of the pressure exerted by the assembly to the skin. In this way, the risk that the assembly could briefly detach from the skin, and/or the risk that the skin is no longer stretched or not optimally stretched at the time that the needle tip touches the skin, is minimized. In other words, the dynamic friction continues to hold the skin in an optimal position at the moment when the needle punctures the skin.

It is noted that this is a distinct difference and advantage over some prior art devices using a spring, because in such devices, there is no mechanism to slow down the acceleration, which may scare the user. Another important difference is that, since there is no spring in the devices of the present invention, the energy for the acceleration is not stored in a spring either. Instead, the energy or force or pressure for accelerating the body 20 and the needle 28 is build-up in a user's forearm and/or hand and/or fingers when pressing the body 20 to the skin. When the static friction is overcome, this force or pressure or energy does not instantly disappear, but decreases only gradually.

Figure 8A:
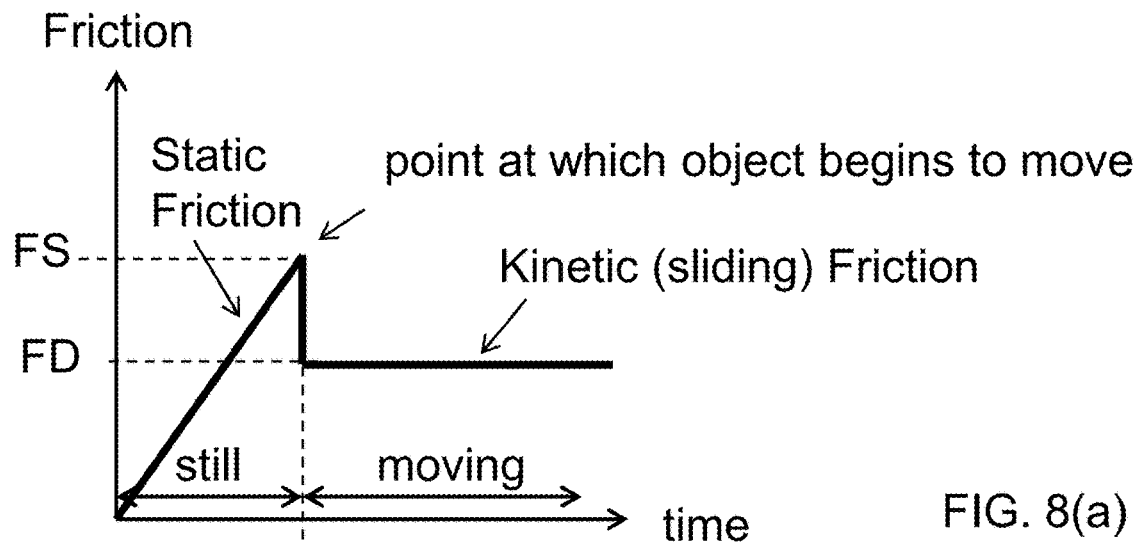
FIG. 8(a) is a typical graph, known per se in the art, showing a typical example of friction between two objects, and shows a typical curve/value of "static friction" and "dynamic friction" (also known as kinetic friction or sliding friction).

FIG. 8(a) is a typical graph, (known per se in the art), showing a typical example of friction between two objects. As can be seen, once the static friction force FS is overcome, the friction force typically drops to a value FD lower than the value FS. The value of FD is typically considered to be substantially constant, and is substantially independent of speed between the two objects (for moderate speeds), assuming that the normal force exerted between both objects is substantially constant.

In the specific example shown in FIG. 5, the inner distance "d3" defined by the grooves 41, 42 remains substantially constant over the distance "d1" to be traveled by the protrusions 21-22, although that is not absolutely required for the present invention to work, and a slightly varying dynamic friction force would probably also work.

FIG. 6 shows a cross-section of the injection device 151 of FIG. 1(a) as seen from the position indicated by "VI" in FIG. 2, perpendicular to the viewing position indicated by "IV" in FIG. 2. Although protrusion 24 is not visible in FIG. 2 (located on the back of FIG. 2), it can be understood that the body 20 also has a second pair 23, 24 of opposite protrusions.

First of all, It is noted that a second set of protrusions is not absolutely required, because the invention would also work with only the first set of protrusions 21, 22, although in that case it would probably be better to provide three protrusions rather than two, for keeping the body in a central position relative to the foot.

Secondly, if present, the second set of protrusions 23, 24 and the corresponding grooves 43, 44 may have exactly the same dimensions at those of the first set of protrusions 21,22 and grooves 41, 42, but that is not absolutely required, and other dimensions d2' and d3' could also be used. Also, even though it would be possible to provide grooves 43-44 having a constant diameter d3' over the entire path to the traveled by the second set of protrusions, in the example shown, dynamic friction is preferably provided over the entire distance "d1" by the first set of protrusions 21, 22, but only over a portion or fraction of the distance "d1" by the second set of protrusions 23, 24. In the specific example shown in FIG. 6 and FIG. 7, the grooves 43, 44 have a diameter d3' smaller than the diameter d2' of the protrusions 23, 24 at an upper portion of the grooves, and have a diameter d4' larger than the diameter d2' defined by the protrusions 23, 24 at a lower portion of the grooves. But other variants are also possible.

FIG. 6(a), and FIG. 7(a), which is an enlarged view of FIG. 6(a) but where some structures like ribs and grooves are not shown in order not to confuse the reader, show the device in the first state, wherein a third and fourth protrusion 23, 24 of the body 20, extending left and right of the body in FIG. 6(a), are in contact with the corresponding grooves 43, 44 (the Protrusions "P" are located above the Edge "E" or 48). This situation is similar to that of FIG. 4(a) and FIG. 5(a).

FIG. 6(b), and FIG. 7(b) which is an enlarged view of FIG. 6(b) but where some structures like ribs and grooves are not shown in order not to confuse the reader, show the device in the second state, wherein the third and fourth protrusion 23, 24 of the body 20, are no longer in contact with the grooves 43, 44.

Thus the second set of protrusions 23-24 and grooves 43-44 contribute to the static friction force, but contribute to the dynamic friction only over part of the distance "d1" to be traveled by the body. In variants of this embodiment, rather than providing only two segments (an upper and a lower) with a single step or edge 48 or "E" in between, multiple segments and multiple intermediate steps could be provided. In yet another variant, the diameter of the grooves 43, 44 could e.g. linearly increase with distance, etc. Many variants of the same principle are possible, and the skilled person having the benefit of the present disclosure may fine-tune the profile of the grooves depending on the application, if so desired.

Figure 8B:
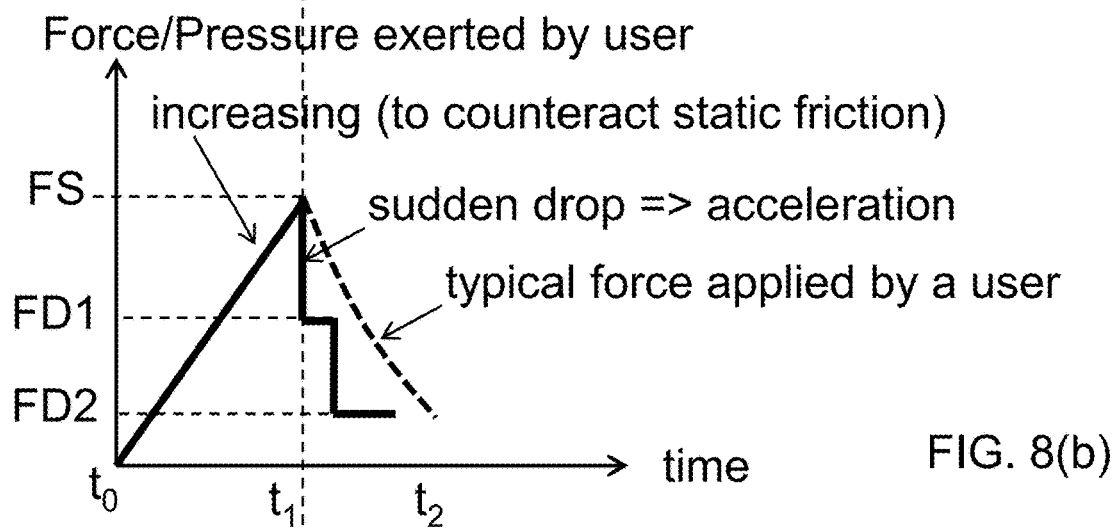
FIGS. 8(b) and (c) is a graph showing how static and dynamic friction are used in the present invention for accelerating the needle.

FIGS. 8(b) and (c) is a graph showing how frictional force is used in the present invention for accelerating the needle 28 and for guaranteeing that the needle 28 penetrates the skin 90 (or at least significantly increases the probability of such penetration).

FIG. 8(b) shows a typical graph of the combined friction forces provided by the first, second, third and fourth protrusion 21-24 versus time, during typical use of the device. First the device is placed on a skin, with the needle in the retracted position (above surface 49). When a user subsequently pushes the body 20 towards the skin 90, initially, as long as the applied force is smaller than the predefined static friction force FS, the body 20 does not move relative to the foot 40. Due to this force or pressure, the foot 40 is pressed towards the skin 90, and in case of flexible or bendable flaps or wings 47, these flaps or wings may expand to further stretch the skin 90. When the applied force has reached the maximum friction force FS, the static friction between all the protrusions 21-24 and their grooves 41-44 is overcome and the body 20 suddenly starts moving, and the total friction force drops to a level FD1, representing the dynamic friction provided by all four protrusions 21-24 moving in their respective grooves 41-44. Shortly after, when the protrusions 23, 24 have moved beyond the edge 48 (shown in FIG. 6(a)), the total friction force drops to a level FD2, representing the dynamic friction provided by the protrusions 21, 22 and the grooves 41-42 only.

FIG. 8(b) shows in dotted line a typical force applied by the user. From time t0 to time t1, the force applied by the user is substantially equal to the static friction force, however, as the body starts to move at time t1, the force applied by the user typically decreases, but this force does not drop to zero instantaneously. The difference between the force applied by the user and the dynamic friction force FD1, FD2 is used mainly to accelerate the needle. (actually the force applied by the user is slightly larger than the static friction force, to bend the flaps or wings if present, and to slightly press the device to the skin, and/or to slightly stretch the skin, but such details are not important for understanding the present invention).

Figure 8C:
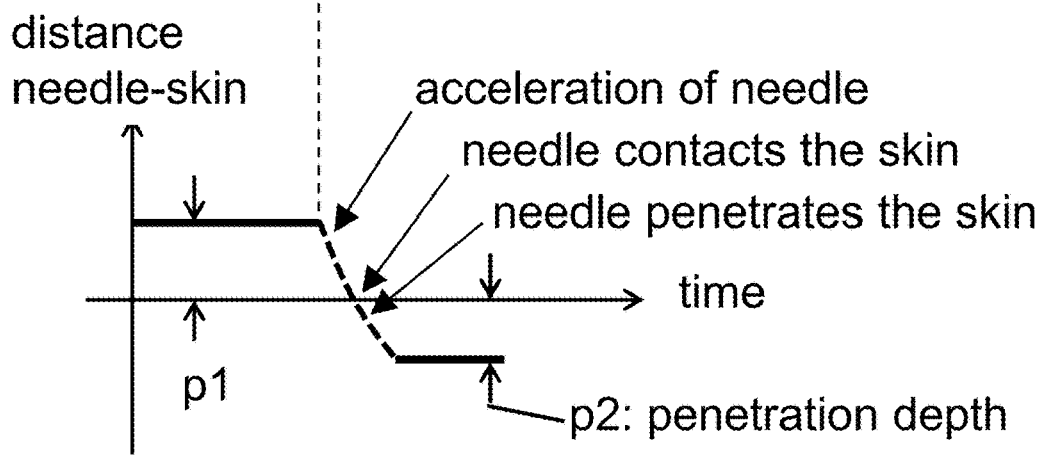
FIG. 8(c) is a typical graph of the distance from the needle tip relative to the skin surface corresponding to the friction forces shown in FIG. 8(b).

FIG. 8(c) is a typical graph of the position of the needle 28 relative to the skin surface corresponding to the friction forces shown in FIG. 8(b). From time t0 to t1, as long as the static friction FS is not overcome, the distance is "p1" (the exact value of which is not critical for the present invention). Then, when the force applied by the user is higher than the static friction FS, the needle 28 suddenly accelerates towards the skin. The exact acceleration profile or speed profile is not important for the present invention to work. What is important is that the needle has gained sufficient speed when contacting the skin, in order to increase the probability that the skin is effectively penetrated.

Everything described above related to the friction forces provided by the protrusions and grooves, works for bodies 20 of the first type (adapted for receiving an existing syringe 50) but also for bodies 60 of the second type (having its proper reservoir and plunger).

In alternative embodiments of the present invention, there may be three or more levels or "steps" in the friction curve of FIG. 8(b), which can be realized e.g. by providing more than one "edge" or "transitions" and/or by using different surface finishing, etc. If the grooves would not have an abrupt change of diameter but a gradual change, the slope of the friction curve would be inclined, etc. The skilled person having the benefit of this disclosure can easily think of other alternatives.

Figures 9A, 9B:
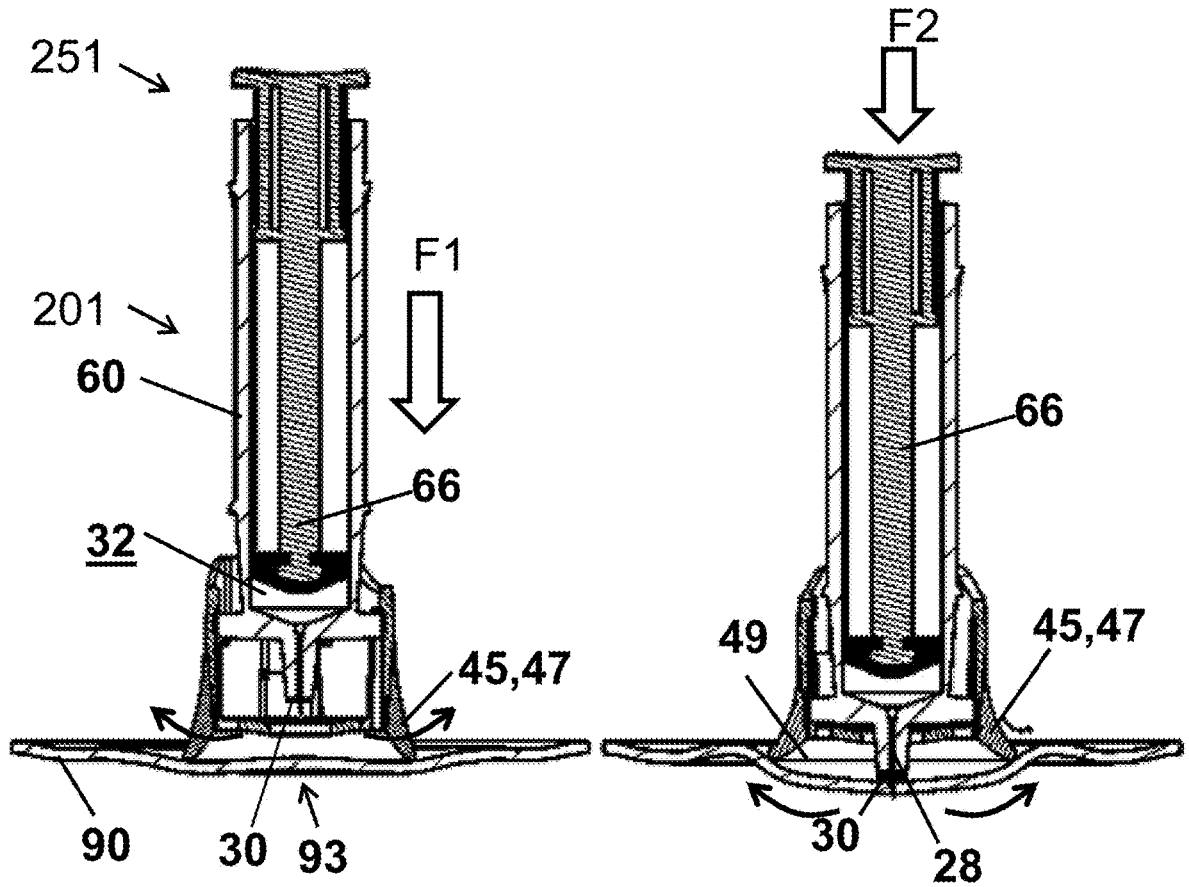
FIG. 9(a) and FIG. 9(b) is a cross sectional view of another injection device according to an embodiment of the present invention, where the assembly has a cylindrical cavity and a plunger. But (although not intrinsically linked)

FIG. 9(a) and FIG. 9(b) show a cross-sectional view of an assembly 201 according to embodiments of the present invention, and an injection device 251 comprising said assembly, to illustrate how a flexible or bendable foot 40 can further stretch the skin. With "further stretch" is meant the additional tensioning due to the deformation of the foot, in addition to the stretching obtained by merely positioning or pushing the foot on the skin). Although illustrated with a body 60 of the second type, stretching of the skin works in exactly the same manner for a body 20 of the first type.

In FIG. 9(a) the injection device 251 is gently positioned on a skin 90. First the skin 90 will be slightly depressed, and a small upward bending bulge 93 will typically occur. If the foot 40 is flexible and/or bendable, the perimeter 45 of the foot, or flaps or wings 47 thereof, will move outwardly when a force F1 is applied to push the assembly 201 to the skin 90, and the outward moving flaps or wings 47 will cause the skin 90 to be slightly stretched further. This stretching puts the skin 90 in a perfect condition of being punctured. When the force F1 further increases to a level at which it overcomes the static friction force FS as described above, the body 60 will suddenly start to move towards the foot, will accelerate, speed will increase, and the needle will penetrate the skin 90. The needle will continue to penetrate the skin 90 until the contact surface 30 (indicated in thick black line for illustrative purposes) comes into contact with the skin 90. In this way a very accurate penetration depth is obtained. When the body 20 has reached its lowest position, the force F1 exerted by the user can be reduced somewhat, and only needs to be sufficient to hold the device in place. The user can now press the plunger 66 to actually inject the fluid in the skin. It may be beneficial to keep the skin stretched by means of the flaps 47 for improving the actual administration and spread of the fluid, but such stretching will typically not influence the penetration anymore.

Figure 10:
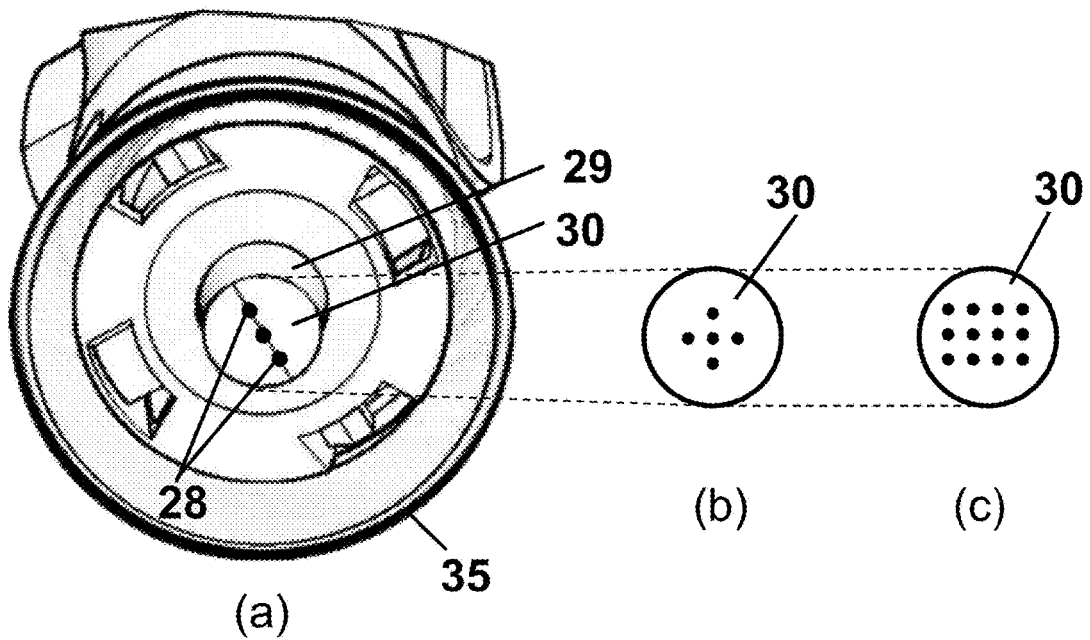
FIG. 10 shows a bottom view the injection device of FIG. 1(b), to illustrate that the injection device of the present invention can also be used with a needle array. The example of FIG. 10(a) shows three needles, the example of FIG. 10(b) shows five needles arranged in a cross, the example of FIG. 10(c) shows a matrix or array of 3×4 needles.

FIG. 10 shows a bottom view of the assembly 102 or the injection device 152 of FIG. 1(b), to illustrate that the injection device 152 of the present invention can also be used with more than one single needle 28, but also works with a plurality of needles, e.g. with five needles arranged in a cross formation as shown in FIG. 10(b), or arranged in a matrix of 3×4 (thus twelve) needles, but other arrangements are also possible, for example a plurality of needles arranged on a circle. Of course, in case more than one needle is used, the grooves 41-44 in the foot 40 (or in the body in alternative embodiments) preferably have a straight axial shape, and not a spiral shape.

The one or more needles may have an inner diameter in the range of 0.0826 mm (34G) to 0.260 mm (26G), but the use of smaller needles may also be possible.

FIG. 11(a) shows an injection device 151 according to embodiments of the present invention, having an assembly 101 and a syringe 50. The syringe 50 comprises a plunger 51. The assembly 101 comprises a body 20 and a foot 40. The body comprises a needle 28 and a cavity 27 in fluid communication with the needle 28. The main purpose of this drawing is to show that the cavity 27 of the body has a conical shape 31 acting as a female connector, being adapted for receiving a syringe 50 with a male protrusion 56, preferably according to the "standard Luer interface".

FIG. 11(b) shows the body 20 of such a device 151 in cross section. Also visible are the ribs 26, which are optionally present.

FIG. 11(c) shows the body 20 in side view.

FIG. 11(d) shows the body of FIG. 11(a) as seen from viewing location "C" (bottom view).

FIG. 12(a) to FIG. 12(c) show a body 60 of the second kind, which is a variant of the body 20 shown in FIG. 11(b) to FIG. 11(d). The body 60 does not have a female connector for receiving a syringe 50, but instead has a cavity 67 forming a reservoir for holding a liquid to be injected. This body 67 can be used for forming a "prefilled injection device".

Figure 13A:
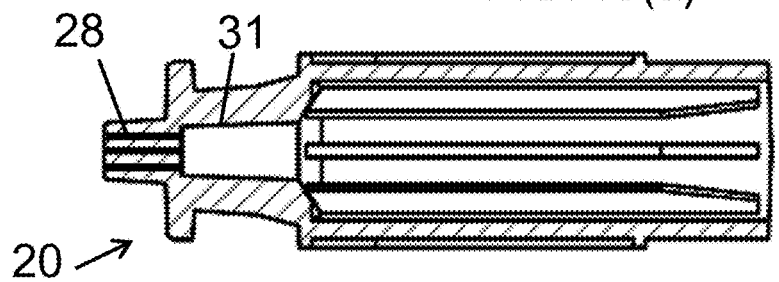
FIG. 13(a) shows the body in cross section, FIG. 13(b) in side view, FIG. 13(c) in bottom view.
Figure 13B:
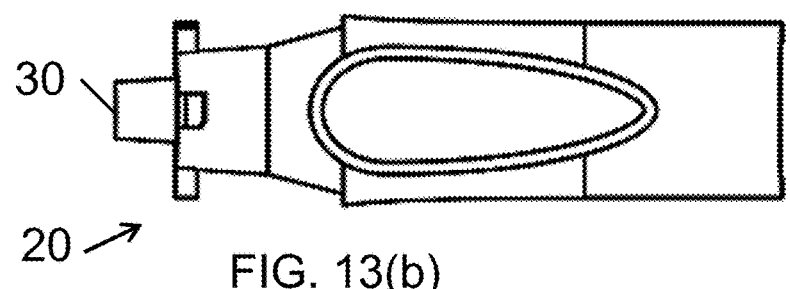
FIG. 13 shows a variant of the body shown in FIG. 11(b) to FIG. 11(d), but having three needles instead of only one.
Figure 13C:
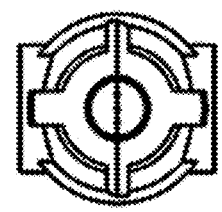

FIG. 13(a) shows a variant of the body shown in FIG. 11. It also has a standard Luer female connector 31 for receiving a syringe 50 (not shown) having a standard Luer male connector. The only difference with the embodiment of FIG. 11(a) is that the body of FIG. 13 has a plurality of needles 28, for example three needles. FIG. 13(b) shows the body 20 in side view, FIG. 13(c) shows the body 20 in bottom view.

Figure 14A:
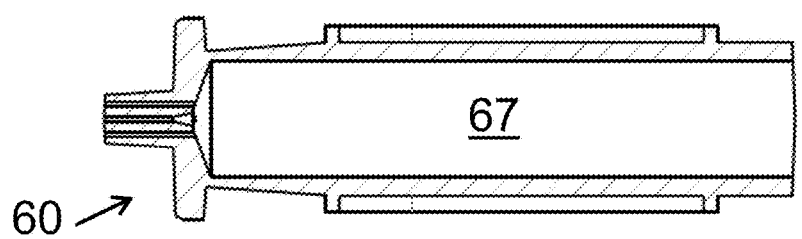
FIG. 14(a) shows the body in cross section, FIG. 14(b) in side view, FIG. 14(c) in bottom view.
Figure 14B:
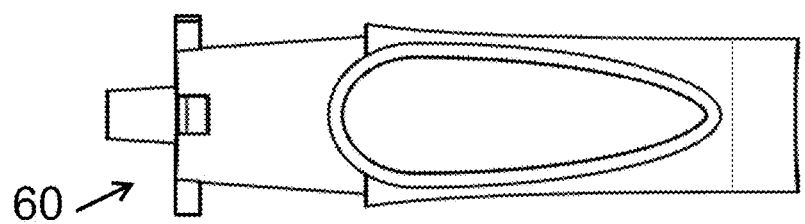
FIG. 14 shows a variant of the body shown in FIG. 12 but having five needles instead of a single needle.
Figure 14C:
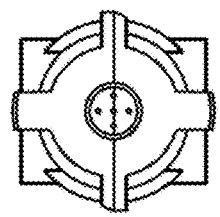

FIG. 14(a) to FIG. 14(c) show a variant of the body shown in FIG. 12, having five needles 28 instead of only one, but of course, the invention is not limited to bodies 60 with only one needle, or with five needles, and another number of needles can also be used, for example 2 or 3 or 4 or more than 5.

Summarizing:

The present invention provides an assembly or actually two versions of an assembly, a first version 101-104 connectable to an existing syringe 50, a second version 201 having its proper reservoir, but the main focus of the present invention is not on the reservoir-side, but on the needle-side.

The assemblies 101-104, 201 of the present invention provide a mechanism for accelerating the needle 28, such that the needle penetrates the skin 90 with speed and impact, thereby increasing the chance of complete penetration of the needle 28 in the skin 90, and reducing or eliminating the risk that the skin is simply pushed down by the needle without actual penetration.

The acceleration mechanism is mainly based on a static friction force FS, which may for example be provided by radially oriented protrusions 21-24 in contact with corresponding grooves 41-44, the protrusions and the grooves having dimensions such that the protrusions are clamped, e.g. radially or circumferentially (not shown). But friction can also be provided in other ways, e.g. by circumferential clamping of protrusions in a groove, or by surface roughness, or in any other suitable way.

The assembly 101-104, 201 does not use a spring or compressed air or the like for generating the sudden acceleration, unlike some prior art devices, but energy or pressure is built-up in a user's finger/hand/fist/muscles. This pressure/force/energy is used to stretch the skin 90 and to accelerate the needle 28 (and the body 20) so that the needle penetrates the skin 90, while keeping the skin stretched using dynamic friction FD.

As explained above, by a simple action of the user, namely by simply placing the assembly on the skin, and simply pushing the assembly towards the skin, the skin will stretch, and the needle will penetrate the skin with almost certainty and to a predefined depth "p2". Then the plunger 51, 66 can be pressed to administer the fluid while holding the assembly against the skin. These actions can be performed using a single hand.

Some of the main advantages offered by an assembly or an injection device according to embodiments of the present invention are: (1) modular approach, ideal for testing various needle designs, (2) can be operated by a single hand, hence is suited for self-administration, (3) no spring or air pressure required, (4) can be used in cooperation with existing syringes, hence can be used to inject about any vaccine or drug etc., (5) very low skill or experience required, (6) needle will almost certainly penetrate the skin to a predefined penetration depth, (7) the main purpose of the dynamic friction FD is to make sure that the skin remains stretched while the needle moves towards the skin. Without the dynamic friction, stretch of the skin could decrease too much, or could perhaps even completely disappear, between the moment at which the needle starts to accelerate and the moment at which the needle actually penetrates the skin, so that the needle would come into contact with a non-stretched or flabby skin.

An assembly according to embodiments of the present invention preferably has a safety lock, which can be unlocked by rotating the foot relative to the body. The safety lock may be an irreversible safety lock to prevent needle stick injuries after use, and to prevent re-use.

The invention claimed is:

1. An assembly for forming an injection device for administering a fluid to a subject, the assembly comprising:
    a foot having a first contact surface adapted to be placed on a skin of the subject, the foot having a tubular shape for receiving a body;
    the body comprising at least one needle fixedly mounted to the body, and comprising a channel in fluid communication with the at least one needle for delivering the fluid to be administered to the subject,
    the body being movably mounted to the foot for allowing movement of the body from a first position in which the needle is in a retracted position not extending out of the first contact surface and not accessible from the outside of the assembly, to a second position in which the needle extends out of said first contact surface and extends out of a second contact surface by a predefined distance for limiting a penetration depth of the needle;
    the assembly further comprising a first friction means for inhibiting movement of the body relative to the foot when the body is in the first position, until a predefined static friction force is overcome, and for causing or allowing a sudden acceleration of the body towards the foot for increasing a speed of the needle for increasing chance of penetration;
    the assembly further comprising a second friction means for creating a predefined dynamic friction force between the foot and the body when the body is moving towards the foot for maintaining contact between the first contact surface of the foot and the skin and for maintaining the skin in a stretched state after the predefined static friction force is overcome, the predefined dynamic friction force being smaller than the predefined static friction force.

2. The assembly of claim 1, wherein an angle between a longitudinal axis of the at least one needle and a tangential plane defined by the first contact surface is a value in the range of 5° to 175°.

3. The assembly according to claim 1, wherein a second contact surface has a disk shape or a dome shape, the at least one needle being positioned in the centre of said disk shape or at a top of the dome shape.

4. The assembly according to claim 3, wherein a predefined distance by which the at least one needle extends out of the second contact surface is a distance in the range of 0.50 to 12.0 mm.

5. The assembly according to claim 3, wherein the at least one needle is a plurality of needles extending from said second contact surface, a number of needles being a value in a range from 2 to 49.

6. The assembly according to claim 1,
    wherein the predefined static friction force is a value in the range from 0.5 to 50.0 Newton; and
    wherein a ratio of the predefined dynamic friction force and the predefined static friction force is a value in the range from 10% to 90%.

7. The assembly according to claim 1, the first friction means comprising:
    at least two protrusions extending from an outer surface of the body being in contact with at least two corresponding grooves located on an inner surface of the foot, wherein a radial dimension defined by the at least two protrusions before assembly of the body and the foot, is larger than a radial dimension defined by the grooves, the static friction being provided by radial clamping; or
    at least two protrusions extending from an inner surface of the foot being in contact with at least two corresponding grooves located on an outer surface of the body, wherein a radial dimension defined by the at least two protrusions before assembly of the body and the foot, is smaller than a radial dimension defined by the grooves, the static friction being provided by radial clamping.

8. The assembly according to claim 7,
    wherein the at least one needle is a single needle, and
    wherein the grooves are at least partly spiral grooves, for rotating the needle when the body is moving towards the foot.

9. The assembly according to claim 1, wherein the body further comprises a cavity in fluid communication with the at least one needle, the cavity being adapted for receiving and accommodating a syringe, the syringe comprising the fluid to be administered and further comprising a plunger movable inside the syringe for forcing the fluid out of the syringe.

10. The assembly according to claim 9, wherein the cavity has a conical channel with standard Luer dimensions for receiving the syringe.

11. An injection device or a kit of parts comprising:
an assembly according to claim 9,
a syringe comprising a plunger, the syringe having an outer diameter smaller than an inner diameter of the cavity.

12. An injection device or a kit of parts according to claim 11, wherein the syringe comprises a fluid to be administered.

13. An injection device or a kit of parts according to claim 11, furthermore comprising a vial containing the fluid to be administered.

14. An injection device or a kit of parts according to claim 13, furthermore comprising a removable needle or other means for extracting the fluid from the vial into the syringe, the removable needle being removable for allowing the syringe to be inserted in the cavity of the body of the assembly.

15. The assembly according to claim 1, wherein the body further comprises a cavity in fluid communication with the at least one needle, the cavity having a tubular shape suitable for containing the fluid to be administered, and suitable for receiving a plunger and for allowing axial movement of said plunger for forcing the fluid out of the cavity.

16. An injection device comprising:
an assembly according to claim 15,
wherein said cavity further comprises the fluid to be administered, and
wherein said cavity further comprises said plunger.

17. The assembly according to claim 1, further comprising a locking mechanism for providing a locked mode and an unlocked mode of the device,
the locked mode being a mode of the assembly, wherein the body is prevented from moving axially to the foot, even when an axial force larger than the predefined static friction force is exerted on the body relative to the foot;
the unlocked mode being a mode of the assembly wherein the body is allowed to move towards the foot, when an axial force larger than the predefined static friction force is applied to the body relative to the foot.

18. The assembly according to claim 1, wherein the foot is at least partly deformable to such an extent that an outer dimension of the first contact surface is capable of increasing by at least 3%, when the foot is being pressed against the skin with a force equal to the predefined static friction force.

19. The assembly according to claim 1, wherein the first friction means does not comprise a spring, and wherein the second friction means does not comprise a spring.

20. The assembly according to claim 1, wherein the predefined dynamic friction force is at least 1 Newton.

* * * * *